US009144605B2

(12) United States Patent
Ikegami et al.

(10) Patent No.: US 9,144,605 B2
(45) Date of Patent: Sep. 29, 2015

(54) RECOMBINANT RIFT VALLEY FEVER VIRUS ENCODING A DOMINANT-NEGATIVE INHIBITOR OF DSRNA-DEPENDENT PROTEIN KINASE IN THE NSS REGION

(71) Applicant: The Board of Regents of the University of Texas System, Austin, TX (US)

(72) Inventors: Tetsuro Ikegami, Galveston, TX (US); Birte Kalveram, Galveston, TX (US); Sabarish Indran, Galveston, TX (US); Olga Lihoradova, Galveston, TX (US); Alexander Freiberg, Galveston, TX (US)

(73) Assignee: The Board of Regents of the University of Texas System, Austin, TX (US)

( * ) Notice: Subject to any disclaimer, the term of this patent is extended or adjusted under 35 U.S.C. 154(b) by 0 days.

(21) Appl. No.: 13/766,941

(22) Filed: Feb. 14, 2013

(65) Prior Publication Data

US 2013/0243815 A1   Sep. 19, 2013

Related U.S. Application Data

(60) Provisional application No. 61/598,673, filed on Feb. 14, 2012.

(51) Int. Cl.
*A61K 39/12*   (2006.01)
*C12N 15/86*   (2006.01)
*A61K 39/00*   (2006.01)

(52) U.S. Cl.
CPC .......... *A61K 39/12* (2013.01); *A61K 2039/5254* (2013.01); *C12N 15/86* (2013.01); *C12N 2760/12034* (2013.01); *C12N 2760/12234* (2013.01)

(58) Field of Classification Search
CPC ........... A61K 39/12; A61K 2039/5254; C12N 2760/12034; C12N 2760/12234; C12N 15/86
See application file for complete search history.

(56) References Cited

PUBLICATIONS

Billecocq et al., 2004, J. Virol. 78(18): 9798-806.
Dungu et al., 2010, Vaccine 28(29): 4581-4587.
Habjan et al. J. Virol. 83(9): 4365-75.
Ikegami and Makino, 2009, Vaccine 27(Suppl. 4): 1-9.
Ikegami and Makino, 2011, Viruses 3(5): 493-519.
Ikegami et al., 2006, J. Virol. 80(6): 2933-2940.
Ikegami et al., 2009, Ann N Y Acad Sci. 1171 (Suppl. 1): E75-E85.
Ikegami et al., 2009, PLoS Pathog. 5(2): 1-17.
Kalveram et al., 2011, J. Virol. 85(13): 6234-6243.
Langland et al., 2006, Virus Res. 119(1): 100-110.
Li and Koromilas, 2001, J. Biol. Chem.
Muller et al., 1995, Am. J. Trop. Med. Hyg. 53(4): 405-411.
Lihoradova et al., 2012, J. Virol. 86(14): 7650-7661.

*Primary Examiner* — Jeffrey Parkin
(74) *Attorney, Agent, or Firm* — Norton Rose Fulbright US LLP

(57) ABSTRACT

Certain embodiments of the invention are directed to methods and compositions comprising a Rift Valley fever virus (RVFV) wherein a heterologous nucleic acid encoding a dsRNA-dependent protein kinase (PKR) inhibitor is inserted into the NSs region of the virus.

9 Claims, 8 Drawing Sheets

RECOMBINANT RIFT VALLEY FEVER VIRUS ENCODING A DOMINANT-NEGATIVE INHIBITOR OF DSRNA-DEPENDENT PROTEIN KINASE IN THE NSS REGION

This application claims priority to U.S. Provisional Application Ser. No. 61/598,673 filed Feb. 14, 2012, which is incorporated herein by reference in its entirety.

STATEMENT REGARDING FEDERALLY FUNDED RESEARCH

This invention was made with government support under 5U54 AI057156 and 1R01 AI057156 awarded by the National Institutes of Health. The government has certain rights in the invention.

REFERENCE TO SEQUENCE LISTING

A sequence listing required by 37 CFR 1.821-1.825 is being submitted electronically with this application. The sequence listing is incorporated herein by reference.

BACKGROUND

Rift Valley fever (RVF) is a mosquito-borne zoonotic disease in humans and ruminants that is caused by the Rift Valley fever virus (RVFV), a member of the family Bunyaviridae, genus Phlebovirus. RVFV causes abortion and fetal malformation in sheep, cattle and goat, while it causes acute febrile illness in humans. Some human patients also develop complications such as neurological disorders, blindness, or lethal hemorrhagic fever. RVFV is classified as category A priority pathogen because of the impact on human health and agriculture.

RVFV has a tripartite negative-stranded RNA genome containing a S-, M- and L-genome segment. The S-segment encodes the N and NSs proteins with the NSs protein encoded in an ambisense manner. The M-segment encodes Gn, Gc, 78-kD, and NSm proteins. The L-segment encodes an RNA-dependent RNA polymerase. The MP-12 strain of RVFV (See GenBank accession No. DQ380154 (S segment), DQ380208 (M segment), and DQ375404 (L segment), each of which are incorporated herein by reference) is one of the most promising vaccine candidates for Rift Valley fever, and the only RVFV strain that is excluded from the select agent rule. MP-12 was generated by serial passages of wild-type ZH548 strain in human diploid MRC-5 cells in the presence of the chemical mutagen 5-fluorouracil. MP-12 is attenuated—having mutations in the M- and L-segment, while the S-segment retains virulence by encoding a functional NSs protein. NSs suppresses host transcription, including interferon-beta (INF-β) mRNA synthesis, and promotes degradation of dsRNA dependent protein kinase (PKR).

Hunter et al. described that pregnant ewes inoculated with live-attenuated MP-12 vaccine strain at 28 to 56 days of gestation caused abortion or teratogenic effects (11 out of 75 lambs from 50 vaccinated ewes), including cerebellar hypoplasia, spinal hypoplasia, hydranencephaly, prognathia inferior, brachygnathia inferior, arthrogryposis, scoiliosis, lordosis, kyphosis, or dormed head. To improve the MP-12 vaccine for both veterinary and human use, additional strains, variants, or modifications are needed.

SUMMARY

The Bunyavirus NSs protein plays an important role in the pathogenesis of Bunyavirus. Expression of the NSs protein in a cell results in (1) the inhibition of interferon production and (2) the degradation of PKR. Deletion or inactivating mutations of NSs result in attenuation of the virus. However, maintenance of the PKR inhibition function enhances stimulation of an immune response to the virus. Thus, the incorporation of PKR inhibition in a NSs inactive virus results in an attenuated virus with an enhance ability to induce an immune response. The viruses described herein preserve the PKR inhibition function without the virulence associated with a NSs expressing virus. Certain embodiments are directed to methods of administering a vaccine in combination with PKR inhibition.

The inventors have discovered that a high level of neutralizing antibodies is induced in mice immunized with an attenuated Bunyavirus in combination with PKR inhibition. In certain embodiments the attenuated Bunyavirus encodes a PKR inhibitor. In certain embodiments, the PKR inhibitor is a dominant-negative PKR. In still a further aspect the dominant-negative PKR is a N167 PKR.

In certain aspects the Bunyavirus is a Phlebovirus. In a further aspect, the Phlebovirus is a Rift Valley fever virus (RVFV), such as an MP-12 strain of RVFV. In a particular aspect, S genome segment is S genome segment encoding N167 PKR. In still a further aspect, the RVFV. In certain aspects, the RVFV is a MP-12 strain of RVFV or a MP-12 N167 RVFV strain. Model animals immunized with a Bunyavirus in combination with inhibition of PKR efficiently accumulated Bunyavirus proteins at the draining lymph node after vaccination. The mice immunized with MP-12 in combination with PKR inhibition obtained the highest level of IFN-α in sera relative to other Bunyavirus treated mice. Therefore, the administration of a PKR inhibitor, such as dominant-negative PKR, or any other molecule that inhibits PKR activity, can increase the immunogenicity of Bunyavirus live-attenuated vaccines.

As used herein, the term "administration" or "administer" or "administering" refers to introducing a composition (e.g., an attenuated Bunyavirus or other therapeutic agent) into the body of a mammal in order to prevent or treat or reduce an infection, a disease, or a condition. Administering "in combination with" one or more further therapeutic agents includes simultaneous (concurrent) and consecutive administration in any order.

Certain embodiments are directed to a Bunyavirus S genome segment comprising a deletion of all or part of the NSs gene or a disruption of the gene by insertion of a heterologous nucleic acid. In certain aspects the S genome segment comprises a heterologous nucleic acid encoding a dominant-negative dsRNA dependent protein kinase (PKR). The deletion of all or part of the NSs gene reduces or abolishes the ability of the NSs protein to inhibit transcription or translation in a host cell. In certain aspects, the S genome segment is a Phlebovirus S genome segment. In a further aspect, the Phlebovirus is Alenquer virus, Candiru virus, Chagres virus, Naples virus, Frijoles virus (FRIV), Punta Toro virus (PTV), Rift Valley fever virus (RVFV), sand fly fever Sicilian virus (SFSV), SFTS virus, or Toscana virus (TOSV).

In certain aspects the S segment or NSs of PTV, FRIV, or SFSV can be specifically excluded as a Phlebovirus S segment or NSs protein of the invention. In certain aspects the heterologous nucleic acid is a TOSV nucleic acid encoding the TOSV NSs protein or variant thereof.

In certain embodiments one or more vector(s) encoding one or more Bunyavirus segments can be an RNA or DNA vector. Certain embodiments are directed to a vector comprising a modified S genome segment. Modification of the S genome segment includes deletion and/or insertion of a heterologous nucleic acid. In a further aspect the vector encoding the S genome segment is a RNA or DNA vector.

Further embodiments are directed to an isolated cell expressing the genome segments described herein.

In certain embodiments, the compositions described herein can be comprised in an immunogenic composition. The immunogenic composition may further comprise an adjuvant.

Certain embodiments are directed to methods of stimulating an immune response in a subject comprising administering an attenuated Bunyavirus in combination with an inhibitor of PKR to a subject. In certain aspects, the PKR inhibitor is encoded by an S genome segment of the Bunyavirus. In a further aspect, the encoded PKR inhibitor is a dominant-negative PKR. In certain aspects, the PKR inhibitor can be a small molecule inhibitor of PKR that is administered in combination with an attenuated Bunyavirus.

The subject can be a human or animal. In certain aspects the term animal includes domestic animals. In a further aspect the animal is a ruminant, such as cattle, goats, sheep, and the like. A ruminant is a mammal that digests plant-based food by initially softening it within the animal's first compartment of the stomach, principally through bacterial actions, then regurgitating the semi-digested mass, now known as cud, and chewing it again.

In still a further embodiment, compositions of the invention can be comprised in a kit.

In certain embodiments there is further provided a method of stimulating an immune response or vaccinating a subject comprising obtaining an immunogenic composition or a vaccine composition according the invention and administering the vaccine composition to a subject. For example, a composition may be administered to a human, however the method may also be used to vaccinate animals such as livestock and animals in zoological gardens. In certain cases, the composition may be administered intravenously, intramuscularly, intraperitoneally, or subcutaneously. In some cases, a composition may be administered multiple times, and in certain cases each administration may be separated by a period of days, weeks, months or years.

In certain aspects an attenuated virus may have reduced virulence or reduced ability to replicate in a subject. In some aspects, for example, an attenuated Bunyavirus will be less pathogenic as compared to a wild type Bunyavirus. In a further aspect the attenuated Bunyavirus will be more immunogenic as compared to wild type or existing vaccine strains of Bunyavirus.

As used herein, an "antigen" refers to a molecule containing one or more epitopes (either linear, conformational or both) that will stimulate a host's immune system to make a humoral and/or cellular antigen-specific response. The term is used interchangeably with the term "immunogen." The term "antigen" includes killed, attenuated, or inactivated viruses.

An "immune response," "immunological response," or "immunogenic response" to a composition is the development in a subject of a humoral and/or a cellular immune response to one or more antigens present in the composition of interest. For purposes of the present invention, a "humoral immune response" refers to an immune response mediated by antibody molecules, while a "cellular immune response" is one mediated by T-lymphocytes and/or other white blood cells.

An "immunogenic composition" is a composition that comprises one or more antigens that upon administration of the composition to a subject results in the development of a humoral and/or a cellular immune response in the subject. The immunogenic composition can be introduced directly into a recipient subject, such as by injection, inhalation, intranasal, or mucosal administration. An "immunogenic composition" also denotes a composition for use in diagnostic assays for detecting the presence of antibodies that bind one or more Bunyavirus antigens.

In certain aspects a deletion of a substantial portion of a viral gene or viral coding region (e.g., the portion of the S segment encoding the NSs protein) includes the deletion of at least 60, 65, 70, 75, 80, 85, 90, 95, 99, or 100% of a gene or the nucleotides encoding a polypeptide or reading frame. Such a substantial deletion will inactivate or effectively reduce the activity of one or more of the genes or gene products having such a deletion. The term effectively reduce refers to the fact that some activity of the gene or gene product having the deletion may be detected but at a level that is not suitable for its physiologic purpose.

"Dominant-negative" refers to a protein that adversely affects the function of the normal, wild-type protein or protein complex. The presence of a dominant-negative protein results in a decrease in the normal function of the wild-type protein or protein complex. A "dominant negative dsRNA dependent protein kinase (PKR)" may be formed by deleting all or part of the kinase domain (e.g., amino acids 242 to 498 of SEQ ID NO:1, See GenBank accession NP_035293.1 for further annotation) or otherwise introducing mutations that reduce the activity of the kinase domain or render the kinase domain inactive, one example of a dominant-negative PKR is illustrated in SEQ ID NO:2. In one aspect PKR has a deletion of amino acid 167 to 515 (i.e., N167 variant). Given the current disclosure one of skill can readily modify PKR and identify those variants that act as dominant-negative PKR inhibitors.

PKR inhibitors refer to molecules that inhibit the activity of PKR. For example, (i) dominant-negative forms of all or part of mammalian PKR (PKR may be derived from different species, including human, sheep, cattle, goat, mouse); (ii) viral proteins and the functional domains thereof that inhibit PKR activity including the subsequent activation of eIF2α (e.g., all or part of Toscana virus NSs protein, Ebola virus VP35 protein, group C rotavirus NSP3 protein, reovirus ρ3 protein, vaccinia virus E3L, K3L proteins, influenza virus NS1 protein, human hepatitis virus NS5A, E2 proteins, human herpes virus-8 vIRF-2, Epstein Barr virus SM protein, herpes simplex virus-1 Us11 protein, Human immunodeficiency virus Tat protein or herpes simplex virus type 1 γ34.5 protein; and (iii) viral RNA that can inhibit PKR activity including Adenovirus VAI RNA or Epstein-Barr virus EBER-1, EBER-2 RNA.

Abbreviations include: RVFV, Rift Valley fever virus; eIF2α, eukaryotic initiation factor 2α; PKR, dsRNA-dependent protein kinase; IRES, internal ribosome entry site; ORF, open reading frame; MEF cells, mouse embryonic fibroblast cells; BSL, biosafety level; DMEM, Dulbecco's modified minimum essential medium; aa, amino acid; IFN, interferon; wt, wild-type; hpi, hours post infection; moi, multiplicity of infection; ActD, actinomycin D; $PRNT_{80}$, 80% Plaque reduction neutralization test.

Other embodiments of the invention are discussed throughout this application. Any embodiment discussed with respect to one aspect of the invention applies to other aspects of the invention as well and vice versa. Each embodiment described herein is understood to be embodiments of the invention that are applicable to all aspects of the invention. It is contemplated that any embodiment discussed herein can be implemented with respect to any method or composition of the invention, and vice versa. Furthermore, compositions and kits of the invention can be used to achieve methods of the invention.

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the standard deviation of error for the device or method being employed to determine the value.

The use of the term "or" in the claims is used to mean "and/or" unless explicitly indicated to refer to alternatives only or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

DESCRIPTION OF THE DRAWINGS

The following drawings form part of the present specification and are included to further demonstrate certain aspects of the present invention. The invention may be better understood by reference to one or more of these drawings in combination with the detailed description of the specification embodiments presented herein.

FIG. 1. Schematic of RVFV MP-12 NSs mutants. Schematic of S-segments of MP-12 and the NSs mutants. The rMP12-C13type (C13type) lacks 69% of NSs ORF as described previously (Muller et al. (1995) *Am J Trop Med Hyg* 53: 405-411). The rMP12-NSsR173A (R173A) encodes an alanine substitution at amino acid 173 of NSs ORF. The rMP12-mPKRN167 (N167) encodes a dominant-negative form of mouse PKR in place of NSs. Expected phenotype corresponding to each S-segment is also presented.

FIG. 2. Induction of IFN-β mRNA and ISG56 mRNA synthesis. Wild-type MEF cells or MEF/PKR$_{0/0}$ cells were mock-infected or infected with MP-12, rMP12-C13type (C13type), rMP12-NSsR173A (R173A), or rMP12-mPKRN167 (mPKRN167) at an moi of 3, and the total RNA were harvested at 7 hpi. Northern blotting was performed with the strand-specific RNA probes to detect mouse IFN-β mRNA, mouse ISG56 mRNA or RVFV antisense S-segment/N mRNA. Both 28S and 18S rRNA stained with ethidium bromide are shown as loading controls.

FIGS. 3A-3B. Host general transcription suppression by RVFV MP-12 mutants. (A) Incorporation of uridine analog, 5-ethynyluridine (EU) into nascent RNA is tested in wt MEF cells. Wildtype MEF cells were mock-infected or infected with MP-12, C31type, R173A, or N167 at an moi of 3, and 1 mM EU was added into culture at 16 hpi for 1 hour. Then cells were fixed and stained with Alexa Fluor 594-coupled azide (red). The cells were further stained with anti-RVFV antibodies, and following Alexa Fluor 488-conjugated anti-mouse IgG (green). As a control, mock-infected cells were co-treated with actinomycin D (ActD) at 5 μg/ml with 1 mM EU for 1 hour at 16 hpi. (B) Fluorescence-activated cell sorting (FACS) analysis was performed in 293 cells. 293 cells were mock-infected or infected with MP-12, C13type or R173A at moi of 3, and treated with 0.5 mM EU at 8 hpi for 1 hour. The control cells were co-treated with ActD (5 μg/ml) at 8 hpi for 1 hour. Incorporated EU was stained with Alexa Fluor 647-azide, and viral antigens were stained with anti-RVFV antibodies. Cells were then analyzed by flow cytometry on the LSRII Fortessa.

FIGS. 5A-5D. Viral N protein accumulation at the draining lymph nodes of mice after immunization. (A) Relative abundance of RVFV N in viral stocks prepared from VeroE6 cells. Representative data from three independent experiments are shown. (B) Five-week-old outbred CD1 mice were mock-immunized with PBS or immunized at the footpad with 1×10$^5$ pfu (30 μl) of MP-12, C13type, R173A, N167, or heat-inactivated MP-12 with 56° C. for 30 min. Popliteal (P) and inguinal (I) lymph nodes were collected at 1 dpi, and the lysates were used for antigen-capture ELISA. The cut-off of 0.104 is shown as a dotted line. (C) Enlarged view of B around the cut-off value. (D) Antigen-capture ELISA was performed by using popliteal and inguinal lymph nodes of mice that were immunized with MP-12 or R173A, collected at 2 and 3 dpi. The cut-off value of 0.145 is shown as a dotted line. MP-12 (NR) represents nonreplicable heat-inactivated MP-12. Asterisk (*) represents statistical significance (Mann-Whitney U-test, p<0.05).

FIGS. 8A-8E. Protection efficacy of MP-12 NSs mutants in mice. Five-week-old CD1 mice were mock-immunized (n=10) or immunized subcutaneously with 1×10⁵ pfu of MP-12 (n=10), C13type (n=10), R173A (n=10), or N167 (n=9). Sera were collected at 42 dpi, and mice were challenged with 1×10³ pfu of wt RVFV ZH501 strain (i.p) at 44 dpi. Mice were observed for 21 days post-challenge. (A) Kaplan-Meier survival curves of immunized mice after wt RVFV challenge. Survival curves of mice were analyzed by logrank (Mantel-Cox) test (vs. mock, $**p<0.01$). (B) Daily weight changes of mock-immunized mice or surviving immunized mice after challenge. (C) $PRNT_{80}$ titers of mice at 42 days post-immunization. (D) Titers of anti-N antibodies in mouse sera at 42 days post-immunization, determined by IgG-ELISA with recombinant RVFV N. Mann-Whitney U-test was performed for statistical analyses ($*p<0.05$, $p<0.01$). (E) Titers of anti-NSs antibodies in mouse sera at 42 days post-immunization and at 21 days post-wt RVFV challenge, determined by IgG-ELISA with NSs carboxy-terminus fused with GST. Cut-off value of 0.144 is shown as a dotted line. Mann-Whitney U-test was performed for statistical analyses of samples (pre vs. post challenge, $p<0.01$). Parentheses show the number of anti-NSs IgG-positive/survivors after wt RVFV challenge.

FIGS. 9A-9C. Generation and characterization of recombinant MP-12 encoding Toscana virus NSs and the mutants in place of MP-12 NSs. (A) Human lung diploid, MRC-5 cells were mock-infected or infected with rMP12-C13type (lacking NSs function), rMP12-TOSVNSs, or rMP12-TOSVNSs-smut-1~15 (mut-1~15) at moi of 3. Total RNA was collected and the accumulation of IFN-b and anti-viral-sense S RNA as well as N mRNA were analyzed by Northern blot. (B) Wild-type mouse embryonic fibroblast (MEF) cells were mock-infected or infected with rMP12-TOSVNSs or mut-1..15 at moi of 3. Accumulation of PKR, RVFV N or b-actin were analyzed by Western blot. (C) Wild-type MEF cells were infected with MP-12, C13type (lacking NSs function), rMP12-TOSVNSs, mut-3 or mut-4 at moi of 0.01. Virus titers at 72 hpi were determined by plaque assay. mut-3: rMP12-TOSNS-K180A/H181A, mut-4: rMP12-TOSNS-H16A/K17A/R18A.

DESCRIPTION

Figures 4A, 4B, 4C, 4D:
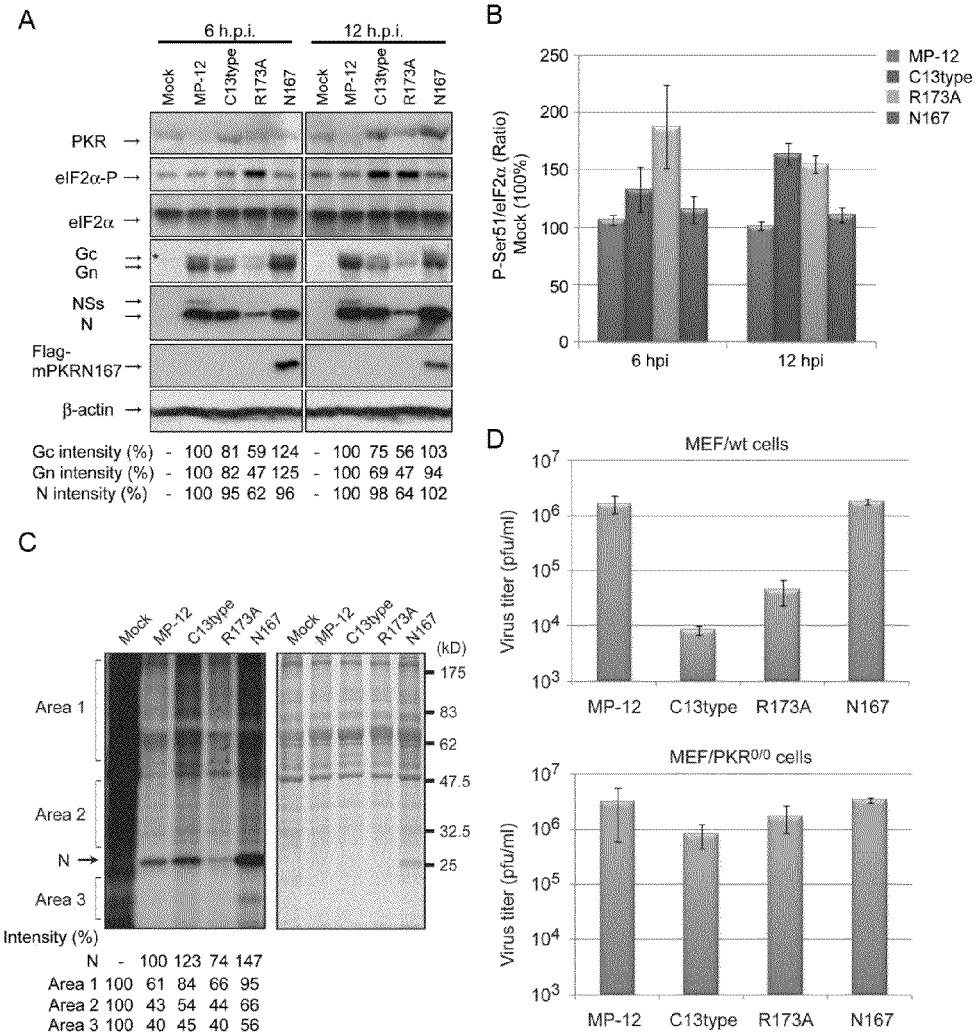
FIGS. 4A-4D. Status of viral translation and replication in wt MEF cells. (A) The status of PKR, eIF2α, and the accumulation of viral N proteins. Wild-type MEF cells were mock-infected or infected with MP-12, C13type, R173A, or N167 at an moi of 3, and the cell lysates were harvested at 6 and 12 hpi. Western blotting was performed to detect PKR, eIF2α, phosphorylated eIF2α (Ser51), viral N and NSs proteins, Flag-mPKRN167, or β-actin (control). Signal intensity of viral proteins (N, Gn and Gc) in cells infected with MP-12 was used as the scale to measure the others and considered as 100%. Data are representative of three independent experiments. (B) The relative abundance of phosphorylated eIF2α. The density of phosphorylated eIF2α normalized to total eIF2α in mock-infected cells is represented as 100%. The mean+/−standard deviation of three independent experiments is shown as graph. (C) Polypeptide synthesis in cells infected with MP-12 mutants. Wildtype MEF cells were mock-infected or infected with MP-12, C13type, R173A, or N167 at an moi of 3, and cells were radiolabeled with 100 μCi/ml of [$^{35}$S] methionine/cysteine for 30 minutes at 16.5 hour post infection (hpi). The total lysates were separated on 10% polyacrylamide gel and analyzed by autoradiography. Intensities of RVFV N or three separate areas (area 1, 2 and 3) are shown at the bottom of left panel. Coomassie blue staining of same samples is shown in the right panel. (D) Replication of MP-12 mutants. Wildtype MEF cells or MEF PKR$_{0/0}$ cells were mock-infected or infected with MP-12, C13type, R173A, or N167 at an moi of 0.01, and culture supernatants were collected at 72 hpi to determine the virus titer by plaque assay on VeroE6 cells. Mean+/−standard deviation of three independent experiments is shown in graph.

Bunyaviridae is a family of vector-borne, negative-stranded RNA viruses generally found in arthropods or rodents. Transmission occurs typically via an arthropod vector—mosquito, tick, or sandfly. Incidence of infection is closely linked to arthropod vector activity, for example, mosquito-borne viruses are more common in the summer. Human infections with certain Bunyaviridae, such as Crimean-Congo hemorrhagic fever virus, are associated with high levels of morbidity and mortality, consequently handling of these viruses must occur with a Biosafety level 4 laboratory. They are also the cause of severe fever with thrombocytopenia syndrome.

The family Bunyaviridae includes the genera: Hantavirus (e.g., Hantaan virus); Nairovirus (e.g., Dugbe virus); Orthobunyavirus (e.g., Bunyamwera virus); and Phlebovirus (e.g., Rift Valley fever virus). Infections with certain Bunyaviridae, cause a number of diseases including: Crimean-Congo hemorrhagic fever and severe fever with thrombocytopenia syndrome.

Bunyaviridae have tripartite genomes consisting of a large (L), medium (M), and small (S) RNA segment. These RNA segments are single-stranded, and exist as ribonucleoprotein (RNP) within the virion. The L segment encodes the RNA-dependent RNA-polymerase, necessary for viral RNA replication and mRNA synthesis. The M segment encodes the viral glycoproteins, which project from the viral surface and aid the virus in attaching to and entering the host cell. The S segment encodes the nucleocapsid protein (N), while the S-segment of the Genera of Orthobunyavirus, Phlebovirus, Tospovirus and some of Hantavirus encode N and nonstructural (NSs) protein. For the Genera of Phlebovirus and Tospovirus, the S segment is ambisense. Ambisense means that some of the genes on the RNA strand are encoded in the negative-sense and others are in positive-sense. The S segment codes for the viral nucleoprotein (N) in the negative-sense and a nonstructural (NSs) protein in positive-sense. Total genome size ranges from 10.5 to 22.7 kbp.

Transcription starts by viral RNA-dependent RNA polymerase (L) binding to a promoter on each encapsidated segment (L, M, and S segment), and is terminated by the unique transcription termination signal at the end of each gene. mRNAs are capped by L protein during synthesis, but are not usually polyadenylated. The S segment ambisense arrangement encodes for several proteins—both genomic and antigenomic RNA are transcribed; two rounds of transcription are required to be carried out. First the negative sense RNA is transcribed to produce mRNA and a full-length replicative intermediate. From this intermediate a subgenomic mRNA encoding the small segment nonstructural protein is produced. The M segment encodes for a polyprotein that is cleaved by a host protease into Gn and Gc proteins. Bunyavirus RNA replicates in the cytoplasm, while the Gn and Gc proteins assembles viral encapsidated RNA and L proteins, and transit through the ER and Golgi apparatus. Mature virions bud from the Golgi apparatus into vesicles that are transported to the cell surface.

The Phlebovirus genus currently comprises over 70 antigenically distinct serotypes, only a few of which have been studied. The 68 known serotypes are divided into two groups: (1) the Phlebotomus fever viruses (the sandfly group, transmitted by Phlebotominae sandflies) comprise 55 members and (2) the Uukuniemi group (transmitted by ticks) comprises the remaining 13 members. Phlebovirus includes, but is not limited to Alenquer virus, Candiru virus, Chagres virus, Naples virus, Punta Toro virus, Rift Valley fever, Sicilian virus, SFTS virus and Toscana virus. Phleboviruses are class V viruses.

Rift Valley Fever is a viral zoonosis (affects primarily domestic livestock, but can be passed to humans) causing fever. It is spread by the bite of infected mosquitoes, typically the Aedes or Culex genera. The disease was first reported among livestock in Kenya around 1915, but the virus was not isolated until 1931. RVF outbreaks occur across sub-Saharan Africa, with outbreaks occurring elsewhere infrequently, but sometimes severely—in Egypt in 1977-78, at least 18,000 people were infected and 598 died during a violent epidemic. In Kenya in 1998, the virus claimed the lives of over 400 Kenyans. In September 2000 an outbreak was confirmed in Saudi Arabia and Yemen.

In humans the virus can cause several syndromes. Usually sufferers have either no symptoms or only a bi-phasic febrile illness with fever, headache, myalgia, and liver abnormalities. Patients who become ill usually experience fever, generalized weakness, back pain, dizziness, and weight loss at the onset of the illness. Typically, patients recover within 2-7 days after onset. In a small percentage of cases (<2%) the illness can progress to hemorrhagic fever, encephalitis, or blindness.

Approximately 1% of human sufferers die of the disease. Amongst livestock the fatality level is significantly higher. In pregnant livestock infected with RVF there is the abortion of virtually 100% of fetuses. An epizootic (animal disease epidemic) of RVF is usually first indicated by a wave of unexplained abortions. Other signs amongst livestock include vomiting and diarrhea, respiratory disease, fever, lethargy, anorexia, and sudden death in young animals. Diagnosis typically relies on viral isolation from tissues, or serological testing with an ELISA.

I. dsRNA-Dependent Protein Kinase (PKR)

dsRNA-dependent Protein kinase also known as protein kinase R (PKR), interferon-induced, double-stranded RNA-activated protein kinase, or eukaryotic translation initiation factor 2-alpha kinase 2 (EIF2AK2) is an enzyme that in humans (see SEQ ID NO:3) is encoded by the EIF2AK2 gene. PKR protects against viral infections.

PKR is activated by double-stranded RNA (dsRNA). PKR contains an N-terminal dsRNA binding domain (dsRBD) and a C-terminal kinase domain. The dsRBD consists of two tandem copies of a conserved double stranded RNA binding motif, dsRBM1 and dsRBM2. PKR is induced by interferon in a latent state. Binding to dsRNA is believed to activate PKR by inducing dimerization and subsequent auto-phosphorylation reactions. In situations of viral infection, the dsRNA created by viral replication and gene expression binds to the N-terminal domain, activating the protein. Once active, PKR is able to phosphorylate the translation initiation factor eIF2α. This inhibits further cellular mRNA translation, thereby preventing viral protein synthesis. Active PKR is also able to mediate the activation of the transcription factor NFκB, by phosphorylating its inhibitory subunit, IκB. Activated NFκB upregulates the expression of Interferon cytokines, which work to spread the antiviral signal locally. Through complex mechanisms, active PKR is also able to induce cellular apoptosis, to prevent further viral spread.

A dominant-negative form of PKR can be engineered by inactivating the c-terminal kinase domain, e.g, SEQ ID NO:2 comprising a C terminal deletion of amino acids 168-515. Inactivation of the kinase domain can be achieved by substitution, deletion, or insertion of nucleotides of the C-terminal kinase domain. In certain aspects, the C-terminal kinase is inactivated by deletion. In a further aspect, substantially all of the kinase domain is deleted. Dominant-negative PKR binds to dsRNA and the subsequent activation of eIF2a can be aborted due to the lack of inactive kinase domain. In certain aspects the dominant negative PKR comprises 10, 20, 30, 40, 50, 60, 70, 80, 90, 100, 110, 120, 130, 140, 150, 160, to 167 consecutive amino acids of SEQ ID NO:2, including all values and ranges there between.

Small molecule inhibitors can also be used in certain aspects of the invention. Small molecule PKR inhibitor include, but is not limited to 2-Aminopurine or imidazole-oxindole PKR inhibitor C16.

II. Formulations and Compositions

In certain aspects a composition component, such as a virus, may be isolated and/or purified from media, and cell or cellular components used to produce the virus. In a method of producing the components of a composition described herein, purification is accomplished by any appropriate technique that is described herein or well known to those of skill in the art (e.g., Sambrook et al., 1987). Although preferred for use in certain embodiments, there is no general requirement that an immunogenic composition of the present invention or a vaccine component always be provided in their most purified state. Indeed, it is contemplated that less substantially purified vaccine component(s), which is nonetheless enriched in the desired component, relative to the natural state, will have utility in certain embodiments. However, it is contemplate that inactive products also have utility in certain embodiments, such as, detecting anti-virus antibodies.

The present invention also provides purified, or substantially purified immunogens or immunogenic components. The term "purified immunogenic component" as used herein, is intended to refer to at least one immunogenic component (e.g., a virus), wherein the component is purified to any degree relative to its naturally obtainable state, e.g., relative to its purity within a cell culture or cellular extract.

Where the term "substantially purified" is used, this will refer to a composition in which the specific component (e.g., a virus) forms the major component of the composition, such as constituting about 50% of the composition or more. In certain aspects, a substantially purified component will constitute more than about 60%, about 70%, about 80%, about 90%, about 95%, about 99% or even more of the composition.

Various techniques suitable for use in chemical, biomolecule, or biological purification, well known to those of skill in the art, may be applicable to preparation of a composition of the present invention. These include, for example, precipitation with ammonium sulfate, PEG, or antibodies, followed by centrifugation; fractionation, chromatographic procedures, including but not limited to, partition chromatograph (e.g., paper chromatograph, thin-layer chromatograph (TLC), gas-liquid chromatography and gel chromatography) gas chromatography, high performance liquid chromatography, affinity chromatography, supercritical flow chromatography ion exchange, gel filtration, reverse phase, hydroxylapatite, lectin affinity; isoelectric focusing and gel electrophoresis (see for example, Sambrook et al. 1989; and Freifelder, Physical Biochemistry, Second Edition, pages 238 246, incorporated herein by reference).

It is contemplated that an immunogenic composition may be combined with one or more additional components to form a more effective composition. Non-limiting examples of additional components include, for example, one or more antigens, immunomodulators, or adjuvants to stimulate or augment or other modulate an immune response to an immunogenic composition. In certain embodiments the additional component can be a PKR inhibitor.

A. Immunomodulators

For example, it is contemplated that immunomodulators can be included in the composition to augment a cell's or a patient's (e.g., an animal's) response. Immunomodulators can be included as purified proteins, nucleic acids encoding immunomodulators, and/or cells that express immunomodulators in the vaccine composition. The following sections list non-limiting examples of immunomodulators that are of interest, and it is contemplated that various combinations of immunomodulators may be used in certain embodiments (e.g., a cytokine and a chemokine).

Cytokines.

Interleukins, cytokines, nucleic acids encoding interleukins or cytokines, and/or cells expressing such compounds are contemplated as possible components of an immunogenic composition. Interleukins and cytokines, include but are not limited to interleukin 1 (IL-1), IL-2, IL-3, IL-4, IL-5, IL-6, IL-7, IL-8, IL-9, IL-10, IL-11, IL-12, IL-13, IL-14, IL-15, IL-18, β-interferon, α-interferon, γ-interferon, angiostatin, thrombospondin, endostatin, GM-CSF, G-CSF, M-CSF, METH 1, METH 2, tumor necrosis factor, TGFβ, LT and combinations thereof.

Chemokines.

Chemokines, nucleic acids that encode for chemokines, and/or cells that express such also may be used as components of an immunogenic composition. Chemokines generally act as chemoattractants to recruit immune effector cells to the site of chemokine expression. It may be advantageous to express a particular chemokine coding sequence in combination with, for example, a cytokine coding sequence, to enhance the recruitment of other immune system components to the site of treatment. Such chemokines include, for example, RANTES, MCAF, MIP 1-alpha, MIP 1-Beta, IP-10 and combinations thereof. The skilled artisan will recognize that certain cytokines are also known to have chemoattractant effects and could also be classified under the term chemokines.

Biological Response Modifiers.

In certain aspects it may be desirable to coadminister biologic response modifiers (BRM), which have been shown to upregulate T cell immunity or downregulate suppressor cell activity. Such BRMs include, but are not limited to, cimetidine (CIM; 1200 mg/d) (Smith/Kline, PA); low dose cyclophosphamide (CYP; 300 mg/m2) (Johnson/Mead, NJ), or a gene encoding a protein involved in one or more immune helper functions, such as B7.

Adjuvants.

Immunization protocols have used adjuvants to stimulate responses for many years, and as such adjuvants are well known to one of ordinary skill in the art. Some adjuvants affect the way in which antigens are presented. For example, the immune response is increased when protein antigens are precipitated by alum. Emulsification of antigens also prolongs the duration of antigen presentation.

Some adjuvants, for example, certain organic molecules obtained from bacteria, act on the host rather than on the antigen. An example is muramyl dipeptide (N acetylmuramyl L alanyl D isoglutamine [MDP]), a bacterial peptidoglycan. The effects of MDP, as with most adjuvants, are not fully understood. MDP stimulates macrophages but also appears to stimulate B cells directly. The effects of adjuvants, therefore, are not antigen specific. If they are administered together with an immunogenic composition, however, they can be used to selectively promote the response to the antigen.

Various polysaccharide adjuvants may also be used. For example, the use of various pneumococcal polysaccharide adjuvants on the antibody responses of mice has been described (Yin et al., J. Biol. Resp. Modif, 8:190-205, 1989). The doses that produce optimal responses, or that otherwise do not produce suppression, should be employed as indicated (Yin et al., J. Biol. Resp. Modif, 8:190-205, 1989). Polyamine varieties of polysaccharides are particularly preferred, such as chitin and chitosan, including deacetylated chitin.

Another adjuvant contemplated for use in the present invention is BCG. BCG (bacillus Calmette-Guerin, an attenuated strain of *Mycobacterium*) and BCG cell wall skeleton (CWS) may also be used as adjuvants in the invention, with or without trehalose dimycolate. Trehalose dimycolate may be used itself. Trehalose dimycolate administration has been shown to correlate with augmented resistance to influenza virus infection in mice (Azuma et al., Cell Immunol., 116(1): 123-134, 1988). Trehalose dimycolate may be prepared as described in U.S. Pat. No. 4,579,945.

Amphipathic and surface active agents, e.g., saponin and derivatives such as QS21 (Cambridge Biotech), form yet another group of adjuvants for use with the immunogens of the present invention. Nonionic block copolymer surfactants (Rabinovich et al., Science, 265(5177):1401-1404, 1994) may also be employed. Oligonucleotides are another useful group of adjuvants (Yamamoto et al., Nature, 334(6182):494-498, 1988). Quil A and lentinen are other adjuvants that may be used in certain embodiments of the present invention.

Excipients, Salts and Auxiliary Substances.

An immunogenic composition of the present invention may be mixed with one or more additional components (e.g., excipients, salts, etc.) that are pharmaceutically acceptable and compatible with at least one active ingredient (e.g., antigen). Suitable excipients are, for example, water, saline, dextrose, glycerol, ethanol and combinations thereof.

A pharmaceutically acceptable salt, includes the acid addition salts (formed with the free amino groups of the peptide) and those which are formed with inorganic acids such as, for example, hydrochloric or phosphoric acid, or such organic acids as acetic, oxalic, tartaric, mandelic, and the like. A salt formed with a free carboxyl group also may be derived from an inorganic base such as, for example, sodium, potassium, ammonium, calcium, or ferric hydroxide, and such organic bases as isopropylamine, trimethylamine, 2 ethylamino ethanol, histidine, procaine, and combinations thereof.

In addition, if desired, an immunogenic composition may comprise minor amounts of one or more auxiliary substances such as for example wetting or emulsifying agents, pH buffering agents, etc. which enhance the effectiveness of the antigenic composition or vaccine.

B. Vaccine Preparations

Once produced and/or purified, a virus or other component may be prepared as a vaccine for administration to a subject. The preparation of a vaccine is generally well understood in the art, as exemplified by U.S. Pat. Nos. 4,608,251, 4,601, 903, 4,599,231, 4,599,230, and 4,596,792, all incorporated herein by reference. In certain embodiments, the compositions of the present invention are prepared to be vaccines.

Vaccine compositions of the present invention comprise an effective amount of one or more Bunyavirus, e.g., Phlebovirus, and/or an additional agent dissolved or dispersed in a pharmaceutically acceptable carrier. The phrases "pharmaceutical or pharmacologically acceptable" refer to molecular entities and compositions that do not produce an adverse, allergic or other untoward reaction when administered to an animal, such as a human. The preparation of an pharmaceutical composition that contains at least one virus or additional active ingredient will be known to those of skill in the art in light of the present disclosure, as exemplified by Remington's Pharmaceutical Sciences, 18th Ed. Mack Printing Company, 1990, incorporated herein by reference. Moreover, for animal (e.g., human) administration, it will be understood that preparations should meet sterility, pyrogenicity, general safety and purity standards as required by FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, *Remington's Pharmaceutical Sciences,* 18th Ed. Mack Printing Company, 1990, pp. 1289-1329, incorporated herein by reference). The vaccine may comprise different types of carriers depending on whether it is to be administered in solid, liquid, or aerosol form, and whether it need to be sterile for such routes of administration as injection. Except insofar as any conventional carrier is incompatible with the active ingredient, its use in the therapeutic or pharmaceutical compositions is contemplated.

An administration schedule and dosages may be varied on a patient by patient basis, taking into account, for example, factors such as the weight and age of the patient, the type of disease being treated, the severity of the disease condition, previous or concurrent therapeutic interventions, the manner of administration and the like, which can be readily determined by one of ordinary skill in the art.

The course of the administration may be followed by assays for antibodies that bind Bunyavirus. These techniques are well known and may be found in a wide variety of patents, such as U.S. Pat. Nos. 3,791,932; 4,174,384 and 3,949,064, as illustrative of these types of assays. Other immune assays can be performed and assays of protection from challenge with the Bunyavirus can be performed, following immunization.

The viruses described herein can be incorporated into diagnostic methods and kits for the detection or production of Bunyavirus and Bunyavirus antibodies. Bunyavirus polypeptides and/or antibodies derived from or by using the compositions described herein can be used in assays to identify Bunyavirus infection, such as RVFV infection. Protein assays include Western blots; agglutination tests; enzyme-labeled and mediated immunoassays, such as ELISAs; biotin/avidin type assays; radioimmunoassays, immunoelectrophoresis; immunoprecipitation, and the like. The reactions generally include labels such as fluorescent, chemiluminescent, radioactive, enzymatic labels or dye molecules, or other methods for detecting the formation of a complex between the peptide and the antibody or antibodies reacted therewith.

The aforementioned assays generally involve separation of unbound antibody or antigen in a liquid phase from a solid phase support to which antigen-antibody complexes are bound. Solid supports that can be used in the practice of some embodiments include substrates or supports such as nitrocellulose (e.g., in membrane or microtiter well form); polyvinylchloride (e.g., sheets or microtiter wells), polystyrene latex (e.g., beads or microtiter plates), polyvinylidine fluoride; diazotized paper; nylon membranes; activated beads, magnetically responsive beads, and the like.

Typically, a solid support is first reacted with a solid phase component (e.g., one or more Bunyavirus viral antigens or antibodies) under suitable binding conditions such that the component is sufficiently immobilized to the support.

After reacting the solid support with the solid phase component, any non-immobilized solid-phase components are removed from the support by washing, and the support-bound component is then contacted with a biological sample suspected of containing the ligand component (e.g., Bunyavirus antigens or antibodies) under suitable binding conditions. After washing to remove any non-bound ligand, a secondary moiety is added under suitable binding conditions, wherein the secondary moiety is capable of associating selectively with the bound ligand. The presence of the secondary binder can then be detected using techniques well known in the art.

III. Examples

The following examples as well as the figures are included to demonstrate preferred embodiments of the invention. It should be appreciated by those of skill in the art that the techniques disclosed in the examples or figures represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

A. Results

Figures 1, 2:
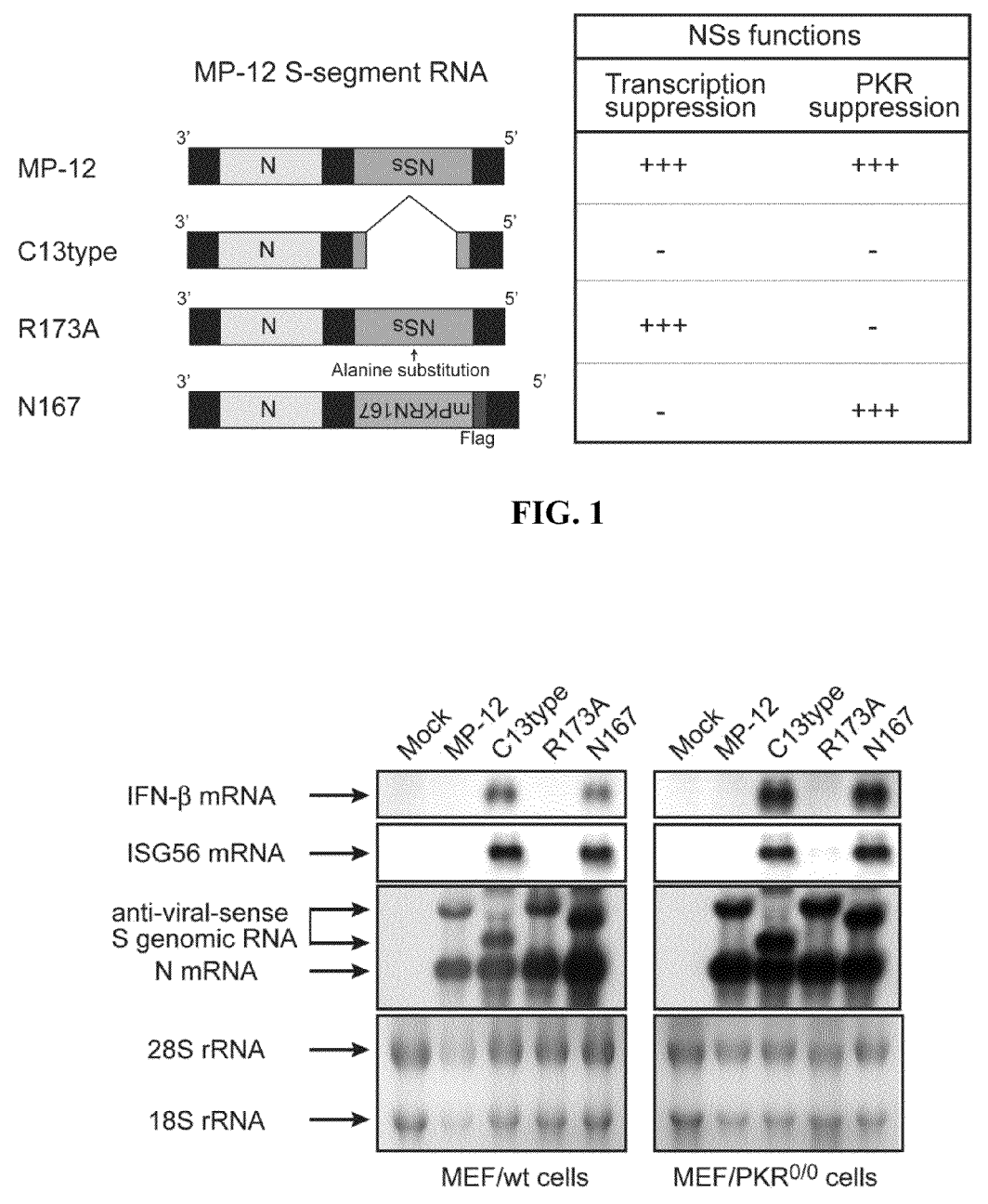

Generation and characterization of recombinant MP-12 to test the NSs functions. To characterize the significance of NSs protein in the immunogenicity of MP-12 vaccine, the inventors first generate recombinant MP-12 with the following NSs functions; (a) no NSs functions, (b) host transcription suppression including IFN-β mRNA synthesis, yet no PKR suppression, and (c) PKR suppression, yet no host transcription suppression including IFN-β mRNA synthesis. The inventors previously generated and characterized rMP12-C13type (C13type), which lacks all the NSs functions by the 69% truncation of NSs ORF (Ikegami et al. (2006) *J Virol* 80: 2933-2940). In preliminary screening process, 14 different NSs mutants were characterized that encode a single alanine substitution at the NSs gene. Among them, rMP12-NSsR173A (R173A) did not degrade PKR and did not induce IFN-β mRNA in infected MRC-5 cells (data not shown). Thus, the inventors further characterized the NSs functions of R173A virus in cell culture. On the other hand, the inventors did not obtain any RVFV NSs mutants that degrade PKR without suppressing host transcription. As an alternative approach, the inventors generated recombinant MP-12 encoding dominant-negative form of mouse PKR in place of MP-12 NSs (rMP12-mPKRN167)(referred to as N167 virus). The inventors used the N-terminus mouse PKR fragment as the dominant-negative mouse (aa.1-167), which is similar to the dominant-negative form of human PKR, PKRΔE7 (Ikegami et al. (2009) *PLoS Pathog* 5: e1000287; Li and Koromilas (2001) *J Biol Chem* 276: 13881-13890). A schematic of recombinant MP-12 S-segments is shown in FIG. 1. At first, the inventors characterized the phenotypes of those mutants in cell culture. To test the ability of mutant MP-12 to suppress IFN-βmRNA synthesis, wild-type (wt) mouse embryonic fibroblast (MEF) cells were mock-infected or infected with MP-12, C13type, R173A, or N167 viruses at moi of 3. The accumulation of mouse IFN-β or ISG56 mRNA was detected by Northern blot as described previously (FIG. 2, Left panel) (Ikegami et al. (2009) *PLoS Pathog* 5: e1000287). Total RNA was extracted at 7 hpi, and Northern blotting was performed with strand-specific RNA probes to detect mouse IFN-β mRNA, mouse ISG56 mRNA, or RVFV anti-sense S-segment/N mRNA. The wt MEF cells infected with C13type or those infected with N167 viruses accumulated detectable IFN-β mRNA and ISG56 mRNA, whereas those infected with MP-12 or R173A virus did not show accumulations of those mRNAs. It is known that PKR activates NF-kB, and induces IFN-β synthesis (Kumar et al (1994) *Proc Natl Acad Sci USA* 91: 6288-6292; Gilfoy and Mason (2007) *J Virol* 81:11148-11158). It was possible that IFN-β mRNA synthesis is mediated by PKR in response to RVFV replication, and the pathway was suppressed by NSs R173A although the PKR is not degraded by NSs R173A. The accumulation of IFN-β mRNA was tested in MEF $PKR_{0/0}$ cells infected with those viruses, which poorly induce IFN-β in response to poly I:C (Yang et al. (1995) *EMBO J* 14:6095-6106). As a result, the inventors found that both MP-12 and R173A could inhibit the IFN-β mRNA synthesis in the absence of PKR (FIG. 2, Right panel). Furthermore, both wt MEF cells and MEF $PKR_{0/0}$ cells infected with N167 virus induced IFN-β mRNA, suggesting that PKR is dispensable for the IFN-β mRNA synthesis in response to RVFV replication. The results suggested that MP-12 and R173A virus can inhibit IFN-β mRNA synthesis independent of the presence of PKR, while C13type and N167 virus fail to suppress IFN-13 mRNA synthesis.

Figures 3A, 3B:
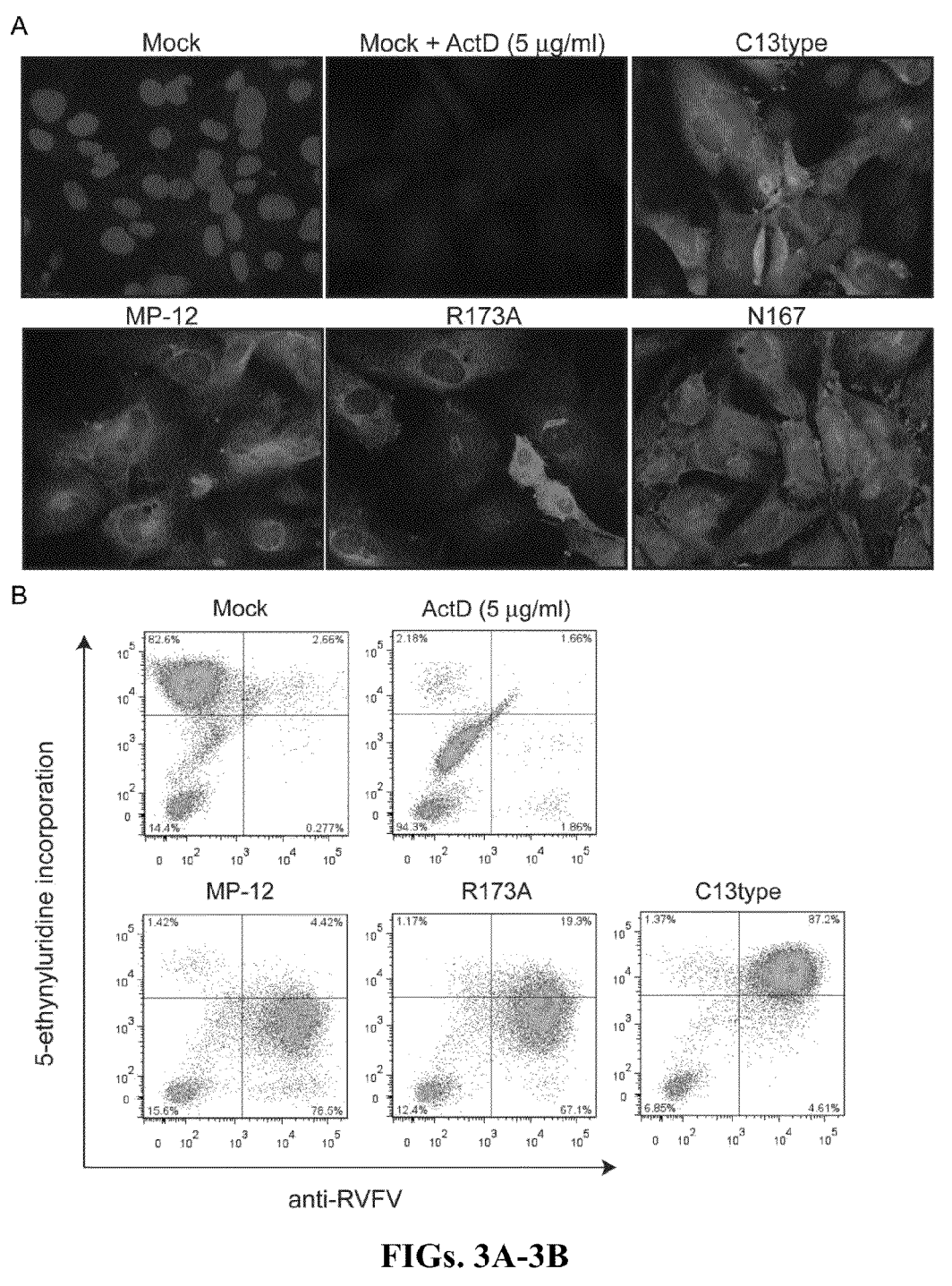

The status of host RNA synthesis was tested in mock-infected wt MEF cells, or those infected with MP-12, C13type, R173A or N167 virus at moi of 3 (FIG. 3A). Cells were treated with uridine analog, 5-ethynyluridine (EU), at 16 hpi, and cells were fixed at 17 hpi. The incorporated EU was covalently linked to Alexa Fluor 594 coupled-azide (producing a red signal) by click reaction, and cells were further reacted with anti-RVFV antibodies (producing a green signal). Mock-infected cells were actively incorporated the EU into nascent RNA in nucleus or nucleoli shown by strong red signals. Such incorporation of EU disappeared in the presence of actinomycin D, suggesting the incorporation of EU is specific to RNA transcription. The cells infected with C13type or N167 actively incorporated EU, while those infected with MP-12 or R173A virus did not incorporate EU as efficiently as those infected with C13type or N167 virus. The results suggested that both MP-12 and R173A suppress host general transcription, while C13type and N167 do not induce host transcription suppression in wt MEF cells.

To better visualize the transcription suppression by R173A NSs, mock-infected 293 cells or those infected with MP-12, C13type or R173A were treated with EU at 8 hpi, fixed at 9 hpi, and stained with Alexa Fluor 647 coupled-azide and anti-RVFV antibody before the analysis with fluorescence-activated cell sorting (FACS) as described previously (FIG. 3B). The result showed that cells infected with R173A can induce host general transcription suppression.

The inventors characterized the status of PKR and eIF2α phosphorylation in wt MEF cells mock-infected or infected with MP-12, C13type, R173A or N167 virus at moi of 3. Cell lysates were collected at 6 and 12 hpi, and Western blot was performed (FIGS. 4A and 4B). Cells infected with MP-12 caused a degradation of PKR at 6 hpi, and phosphorylation status of eIF2α was not significantly changed. Cells infected with C13type slightly increased the abundance of PKR at 12 hpi, and induced phosphorylation of eIF2α around 12 hpi. As a result, the accumulation of Gn and Gc were decreased by 20 to 30%, while that of N was not significantly changed. On the other hand, cells infected with R173A did not degrade or increase PKR, while induced eIF2α phosphorylation at 6 hpi and 12 hpi, and the accumulation of Gn, Gc, and N proteins were markedly decreased. Cells infected with N167 virus increased the abundance of PKR, while not increasing the phosphorylated eIF2α, suggesting the mouse PKR N167 works as dominant-negative in PKR-mediated eIF2α phosphorylation pathway.

To know the cellular translation activity at late time point after infection, cellular polypeptide synthesis was tested between 16.5 hpi and 17 hpi in wt MEF cells mock-infected or infected with MP-12, C13type, R173A, or N167 virus at moi of 3 (FIG. 4C). Cells infected with MP-12 or R173A suppressed 40 to 60% of host polypeptide synthesis, while the cells infected with MP-12 supported better N protein synthesis than those infected with R173A. Cells infected with C13type showed about 5 to 20% better synthesis of host polypeptides, and showed active viral N protein synthesis. Cells infected with N167 virus maintained high level of cellular translation with approximately 10% higher than that of C13type-infected cells, and showed the most active N protein synthesis at the indicated time frame. The result suggests that the combination of host transcription suppression and viral replication induces the suppression of host protein synthesis, while the degradation of PKR supports viral protein synthesis of MP-12, which is consistent with previous study (Ikegami et al. (2009) *PLoS Pathog* 5: e1000287). On the other hand, it was also suggested that cells with active host transcription do not induce the shut-off of host and viral translation even eIF2α is induced by RVFV replication.

Viral replication level of MP-12, C13type, R173A or N167 virus were tested in wt MEF cells at 72 hpi with moi of 0.01 (FIG. 4D, top panel). The indicated time point was selected because previous kinetics study suggested that 72 hpi is one of the peak time points which is appropriate to evaluate the ability of viral replication among MP-12 NSs mutants in type-1 IFN competent cells (Ikegami et al. (2006) *J Virol* 80: 2933-2940. MP-12 and N167 virus reached to more than $1\times10^6$ pfu/ml at 72 hpi, while C13type or R173A replicated up to $8\times10^3$ or $4.5\times10^4$ pfu/ml, respectively. Because both C13type and R173A, which induced eIF2α phosphorylation, showed reduced viral titer in wt MEF cells, the inventors suspected the role of PKR-mediated eIF2α phosphorylation in virus replication, and tested viral replication in MEF $PKR_{0/0}$ cells, which lack active PKR (FIG. 4D, bottom panel). In MEF $PKR_{0/0}$ cells, all the tested viruses including C13type and R173A replicated nearly $1\times10^6$ pfu/ml, suggesting that PKR-mediated eIF2α phosphorylation affects on efficient RVFV replication in cell culture.

Impact of NSs on Viral Protein Accumulation at Draining Lymph Nodes in Mice.

Figures 5A, 5B, 5C, 5D:
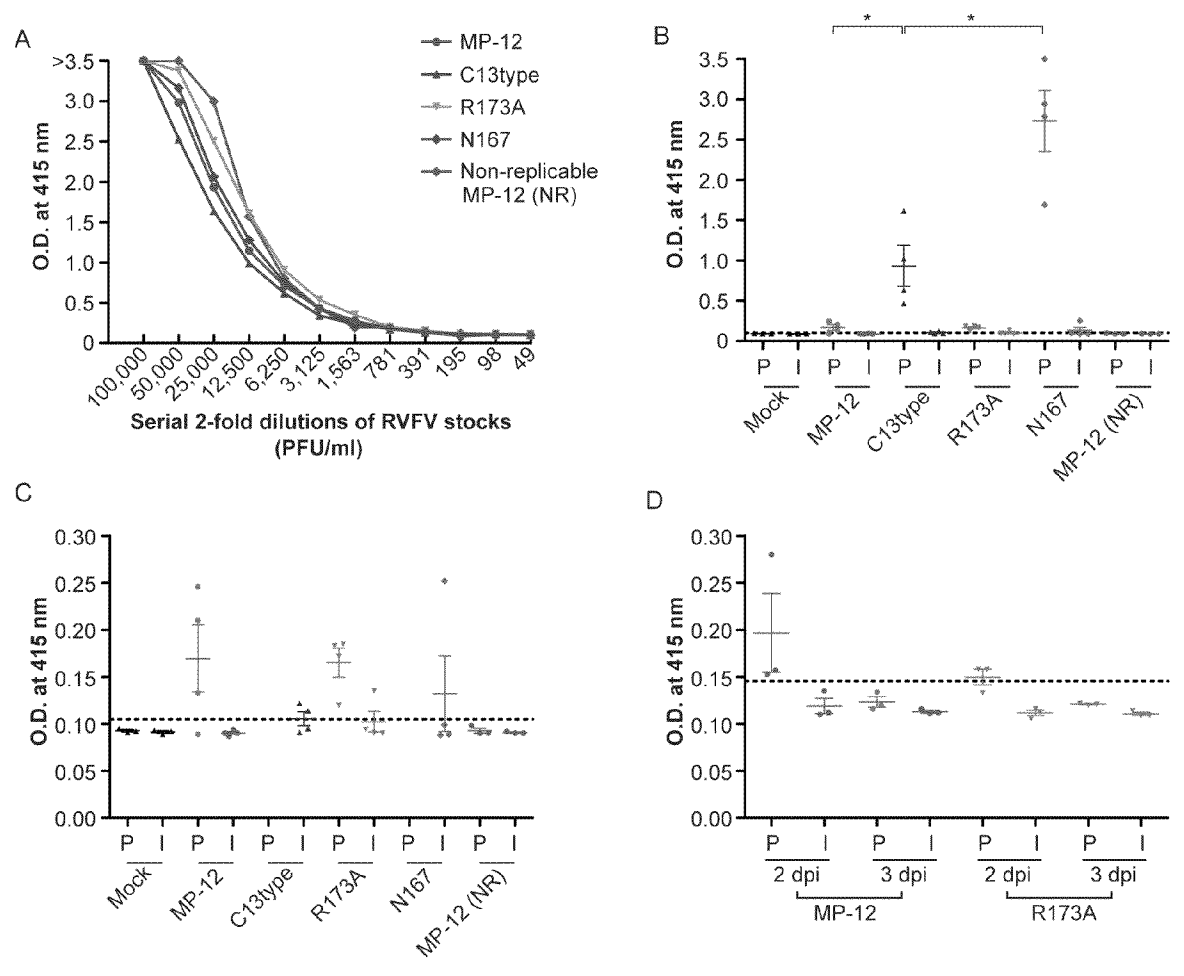

Although PKR suppression promotes the viral protein accumulation in wt MEF cells, it is unclear whether the accumulation is important for host immune response. After subcutaneous immunization, the first tissue that serves as adaptive immune response is the local draining lymph nodes. To understand the significance of NSs functions in the adaptive immune response, the abundance of RVFV N antigens were characterized at the draining lymph nodes (i.e., popliteal and inguinal lymph nodes) downstream of the footpad after footpad inoculation via s.c. At first, the inventors analyzed the abundance of RVFV N antigens in each virus inoculum by antigen-capture enzyme-linked immunosorbent assay (ELISA) that can specifically detect RVFV N. FIG. 5A shows the OD values of virus inocula containing each MP-12 mutants including inactivated MP-12 as non-replicable virus control. The abundance of N differed significantly if the viruses were derived from different cell substrates (e.g. VeroE6 cells and MRC-5 cells) (data not shown), while it was relatively similar if those viruses were derived from the same type of cells (FIG. 5A). Both popliteal and inguinal lymph nodes were collected at 1 dpi, and the whole lysates were tested with antigen capture ELISA (FIG. 5B). RVFV N was abundantly detected in popliteal lymph nodes from mice immunized with C13type or N167, whereas it was not detected in inguinal lymph node from the same mice. On the other hand, RVFV N was not detected in either popliteal lymph nodes or inguinal lymph nodes from mice immunized with MP-12, R173A or heat-inactivated nonreplicable MP-12. Mice immunized with MP-12 or R173A did not accumulate RVFV N at 2 dpi and 3 dpi (FIG. 5C), suggesting that NSs-mediated transcription suppression leads to poor accumulation of viral antigens at the draining lymph nodes. The N accumulation at popliteal lymph node was more abundant in mice immunized with N167 virus than those immunized with C13type, suggesting that the suppression of PKR in the absence of host transcription suppression promotes the accumulation of viral proteins at the draining lymph node.

Host Immune Responses to MP-12 NSs Mutants.

Figure 6:
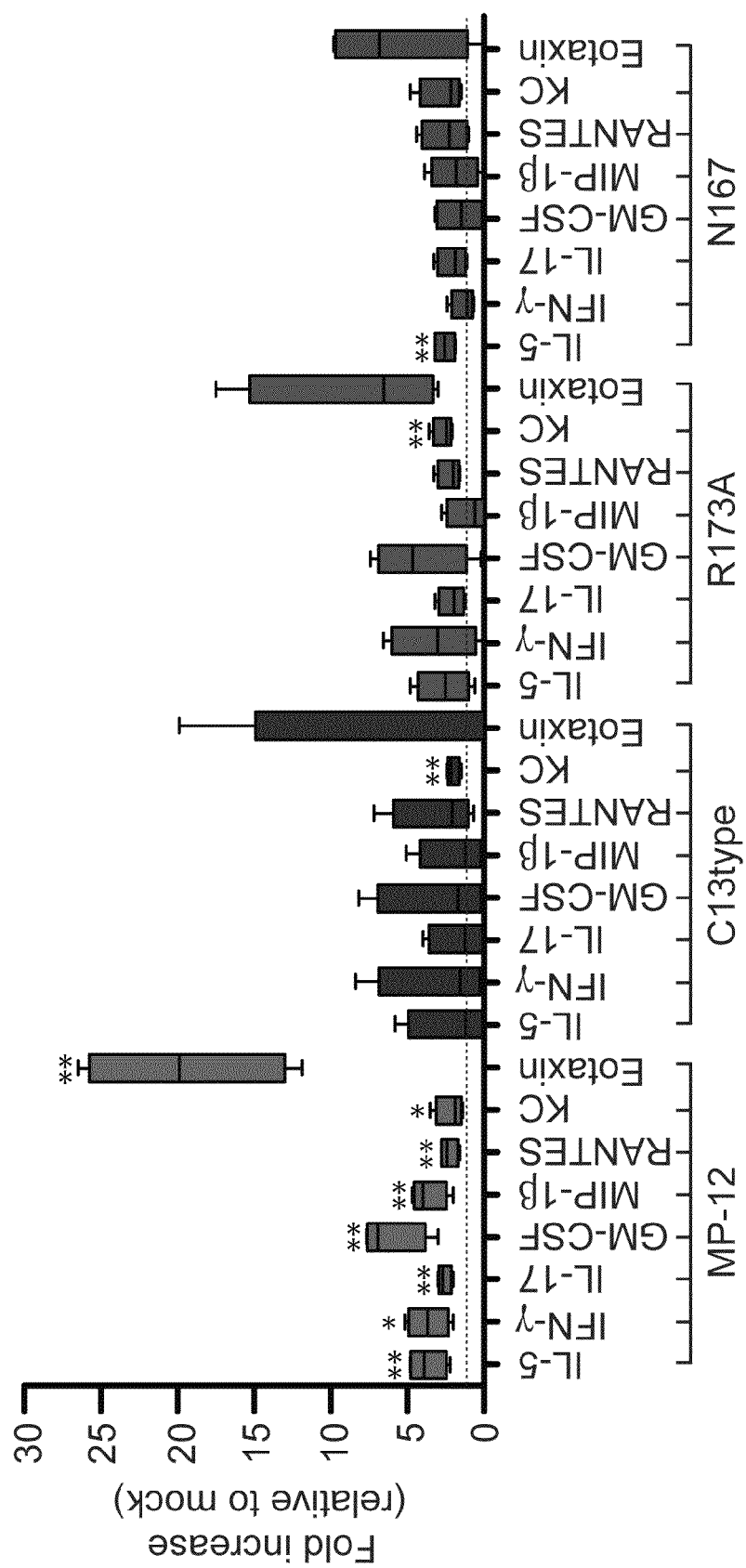
FIG. 6. Measurement of cytokines and chemokines in the sera of immunized mice. Five-week-old CD1 mice were mock-immunized with PBS (n=3) or immunized at the footpad with 1×10⁵ pfu (30 μl) of MP-12, C13type, R173A, or N167 (n=4). Sera were collected at 2 dpi, and the abundance of cytokines and chemokines was measured by using the Bio-Plex Pro Mouse Cytokine 23-Plex Assay (BioRad). The fold-increases relative to the highest value of mock samples are shown. Unpaired student's t-test (vs. mock-immunized) was performed for statistical comparison ($*p<0.05$, $**p<0.01$).

To understand early host responses to MP-12 and the mutants, the cytokine and chemokine level were directly analyzed in the mouse sera at 2 dpi at which time point MP-12 or R173A escaping from draining lymph node might establish secondary infection. Outbred CD1 mice were immunized via s.c. at the footpad with PBS or $1 \times 10^5$ pfu of MP-12, C13type, R173A or N167, and sera were collected at 2 dpi. Serum cytokines were detected with Bio-Plex Pro Mouse Cytokine 23-Plex Assay. The inventors observed statistically significant increase in IL-5, IFN-γ, IL-17, GM-CSF, MIP-1β, RANTES, KC and Eotaxin in mice immunized with MP-12 compared to mock control (FIG. 6). On the other hand, the inventors did not observe such consistent increase in mice immunized with C13type, R173A, or N167. The results suggested that MP-12 is recognized by host immune system although MP-12 proteins were not accumulated at the draining lymph nodes.

Figures 7A, 7B, 7C:
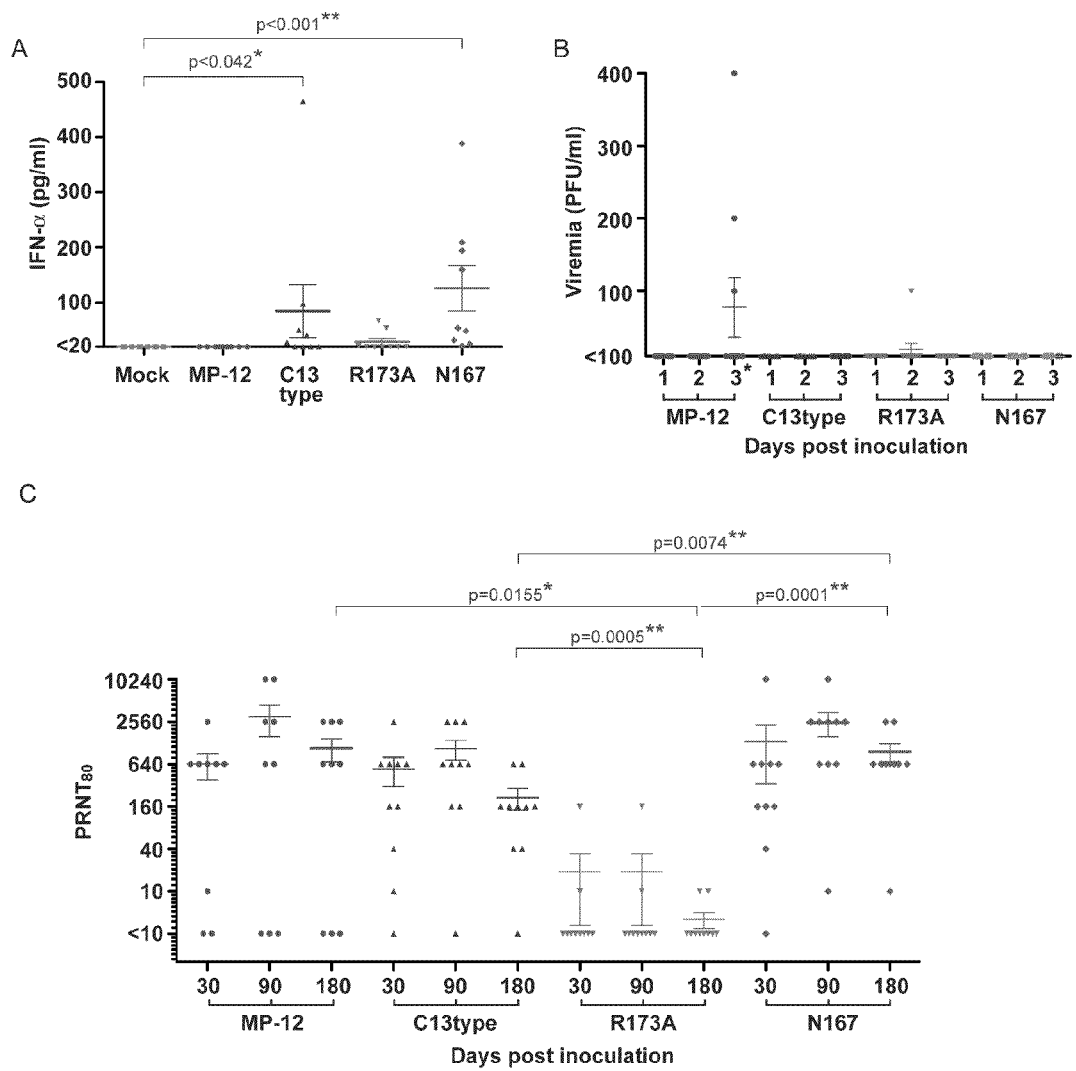
FIGS. 7A-7C. IFN-α, viremia and neutralizing antibody production in mice infected with MP-12 NSs mutants. Five-week-old CD1 mice were mock-immunized with PBS (n=6) or immunized subcutaneously with 1×10⁵ pfu of MP-12, C13type, R173A, or N167 (n=9). Sera were collected at 1, 2, 3, 30, 90, and 180 dpi. (A) Abundance of IFN-α in mouse serum samples (n=6: mock, n=9: other groups) at 1 dpi. Serum IFN-α was measured by the VeriKine Mouse Interferon Alpha ELISA Kit (pbl international source). Mann-Whitney U-test was performed for statistical analyses ($*p<0.05$, $**p<0.01$). (B) Viral titer of mouse serum samples (n=10 per group). The viral titers in serum samples at days 1, 2, and 3 were determined by plaque assay in VeroE6 cells. Asterisk (*) represents $p<0.05$ (vs. other groups except for R173A 2 dpi) by Kruskal-Wallis test. (C) Neutralizing antibody titers of serum samples: MP-12 (n=9), C13type (n=10), R173A (n=10), or N167 (n=10). Plaque-reduction neutralization test ($PRNT_{80}$) was performed to determine the neutralizing antibody titer. Mann-Whitney U-test was performed for statistical analyses between $PRNT_{80}$ titers at 180 dpi ($*p<0.05$, $**p<0.01$).

The inventors initial characterization of MP-12, C13type, R173A and N167 virus in MEF cells suggested that both MP-12 and R173A can inhibit host transcription including IFN-β mRNA synthesis (FIGS. 2 and 3), while the eIF2α phosphorylation lead to the reduction in virus titer of C13type and R173A in wt MEF cells (FIG. 4D). To confirm the consistency of NSs functions between cell culture and in vivo, the induction of IFN-α and viremia were tested after immunization. Mice were subcutaneously immunized with PBS or $1 \times 10^5$ pfu of MP-12, C13type, R173A or N167. IFN-α in the sera at 1 dpi was tested by VeriKine Mouse Interferon Alpha ELISA Kit (Cat #42120, pbl international). The IFN-α was detected in 0%, 55%, 33% or 100% of mice immunized with MP-12, C13type, R173A, or N167 virus, respectively (FIG. 7A). Viremia level in sera at 1, 2, and 3 dpi was tested by plaque assay with VeroE6 cells. Three of ten mice immunized with MP-12 developed viremia of 100 to 400 pfu/ml at 3 dpi, while one of ten mice immunized with R173A developed viremia of 100 pfu/ml at 2 dpi (FIG. 7B). No mice immunized with C13type or N167 virus showed detectable viremia, although N167 could replicate efficiently in wt MEF cells, suggesting highly efficient host defense mechanism to suppress viral replication in response to type-I IFN in vivo. It was evident that NSs-mediated transcription suppression by MP-12 inhibits the induction of type-I IFN after immunization, and lead to viremia, while mice immunized with R173A did not suppress IFN-α induction efficiently in mice, suggesting that poor synthesis of NSs proteins of R173A virus in infected cells lead to insufficient suppression of host type-I IFN mRNA synthesis in vivo.

To understand the stimulation of B cell responses, neutralizing antibody development of those mice at day 30, day 90 and day 180 was tested (FIG. 7C). Six of 9 (66%) mice immunized with MP-12 developed neutralizing antibodies (NAb) of 1:640 or higher at 90 dpi and maintained the high NAb titers until day 180; while 9 of 10 (90%) mice immunized with C13type developed NAb of 1:40 or higher at 90 dpi, and maintained it until day 180. On the other hand, 2 of 10 (20%) of mice immunized with R173A developed NAb (1:10 and 1:160) at 30 dpi, and the 1:160 of NAb was decreased to 1:10 at 180 dpi. All the mice immunized with N167 raised NAb at 1:640 or higher at 90 dpi except for 1 mouse with NAb titer of 1:10. The results suggest that a lack of host transcription suppression function of NSs does not have an affect on the development of NAb in mice, while the lack of PKR degradation function abolishes the ability to induce NAb by MP-12 as shown in R173A. When PKR suppression function is given to MP-12 lacking NSs, the mean titer of NAb was significantly increased. Thus, it was suggested that host transcription suppression function is dispensable for NAb development, while the PKR degradation function is indispensable for NAb development when host transcription is suppressed by MP-12 NSs.

Role of NSs Functions in the Efficacy of Vaccine.

Figures 8A, 8B, 8C, 8D, 8E:
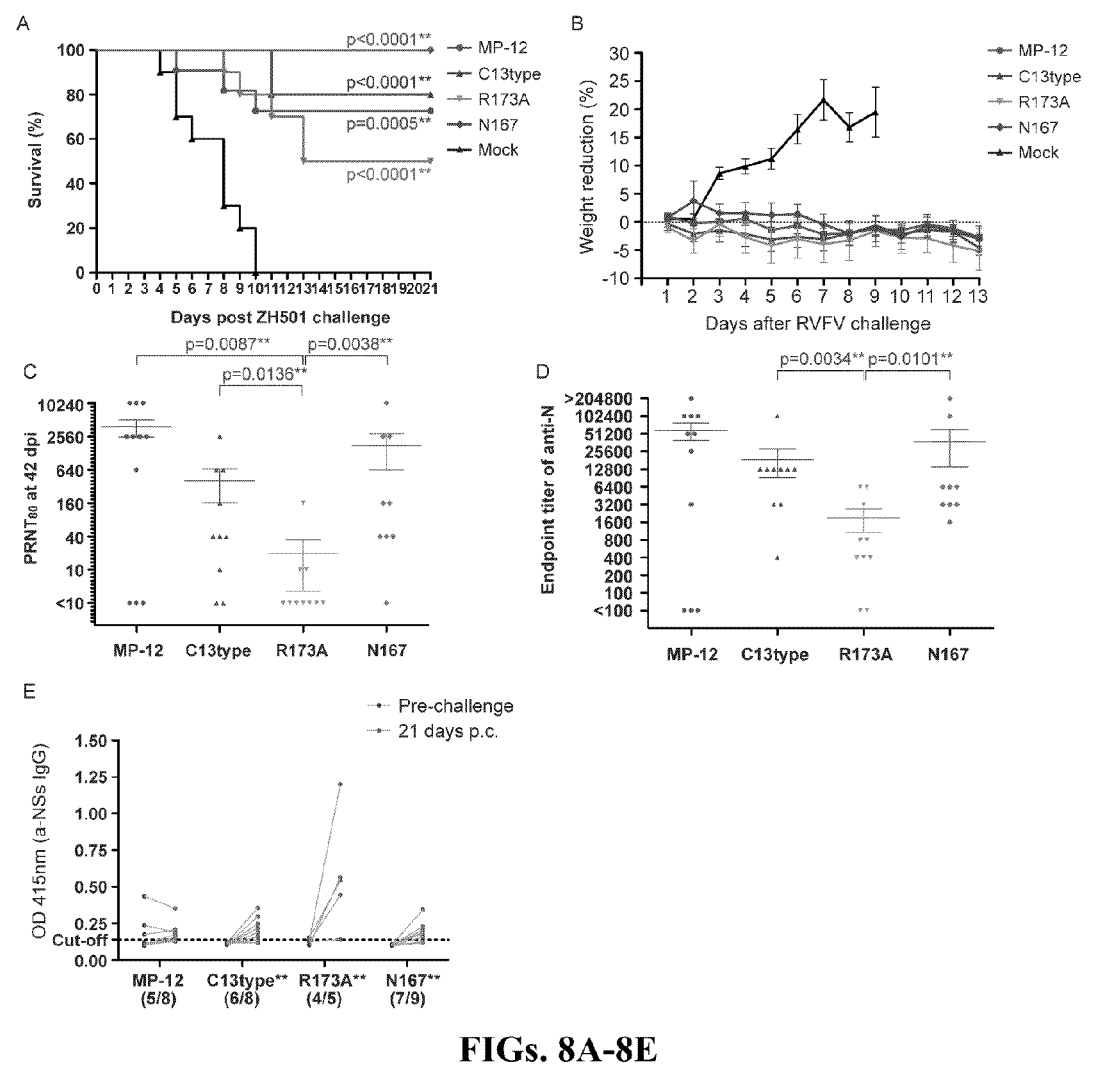

The inventors tested the efficacy of MP-12 mutants in mice by challenging with wt RVFV ZH501 strain. Outbred CD1 mice were mock-immunized with PBS or immunized with $1 \times 10^5$ pfu of MP-12, C13type, R173A, or N167 subcutaneously. At 42 dpi, sera were collected, and the titers of NAb were determined (FIG. 8A). The result of NAb titration was largely consistent with FIG. 6C, and 73%, 80%, 30% or 89% of mice immunized with MP-12, C13type, R173A or N167 developed NAb of 1:10 or higher, respectively. Then, mice were challenged at 44 dpi with $1 \times 10^5$ pfu of wt RVFV ZH501 (i.p). Mock-immunized mice were all dead in 10 days, while 72%, 80%, 50% or 100% of mice immunized with MP-12, C13type, R173A, or N167 were protected from the challenge, respectively (FIG. 8B). The daily weight change showed continuous decrease in body weight in mock-immunized mice, while surviving mice immunized with MP-12, C13type, R173A, or N167 did not show any marked decrease in body weight after wt RVFV challenge (FIG. 8C). Importantly, all the immunized mice that were dead after challenge lacked detectable NAb in sera at 42 dpi. The results suggest that NAb plays an important role for protecting immunized animals from wt RVFV challenge. On the other hand, it was noted that 2 mice immunized with R173A or 1 mouse immunized with N167 survived without detectable NAb. The sera were further analyzed with IgG-ELISA system to detect anti-N specific antibodies. As a result, it was found that those 3 survivors had detectable anti-N antibodies (FIG. 8D). The inventors also observed that all the mice immunized with C13type or N167 had detectable anti-N antibodies, suggesting that anti-N antibody is not responsible for the protection of animals. It was found that 3 mice immunized with MP-12 and 2 mice immunized with R173A, which lacked detectable NAb, did not have anti-N IgG. The results indicated that MP-12 or R173A, which inhibit host transcription, might have a tendency to generate non-responders to vaccination in outbred populations through subcutaneous inoculation.

Figures 9A, 9B, 9C:
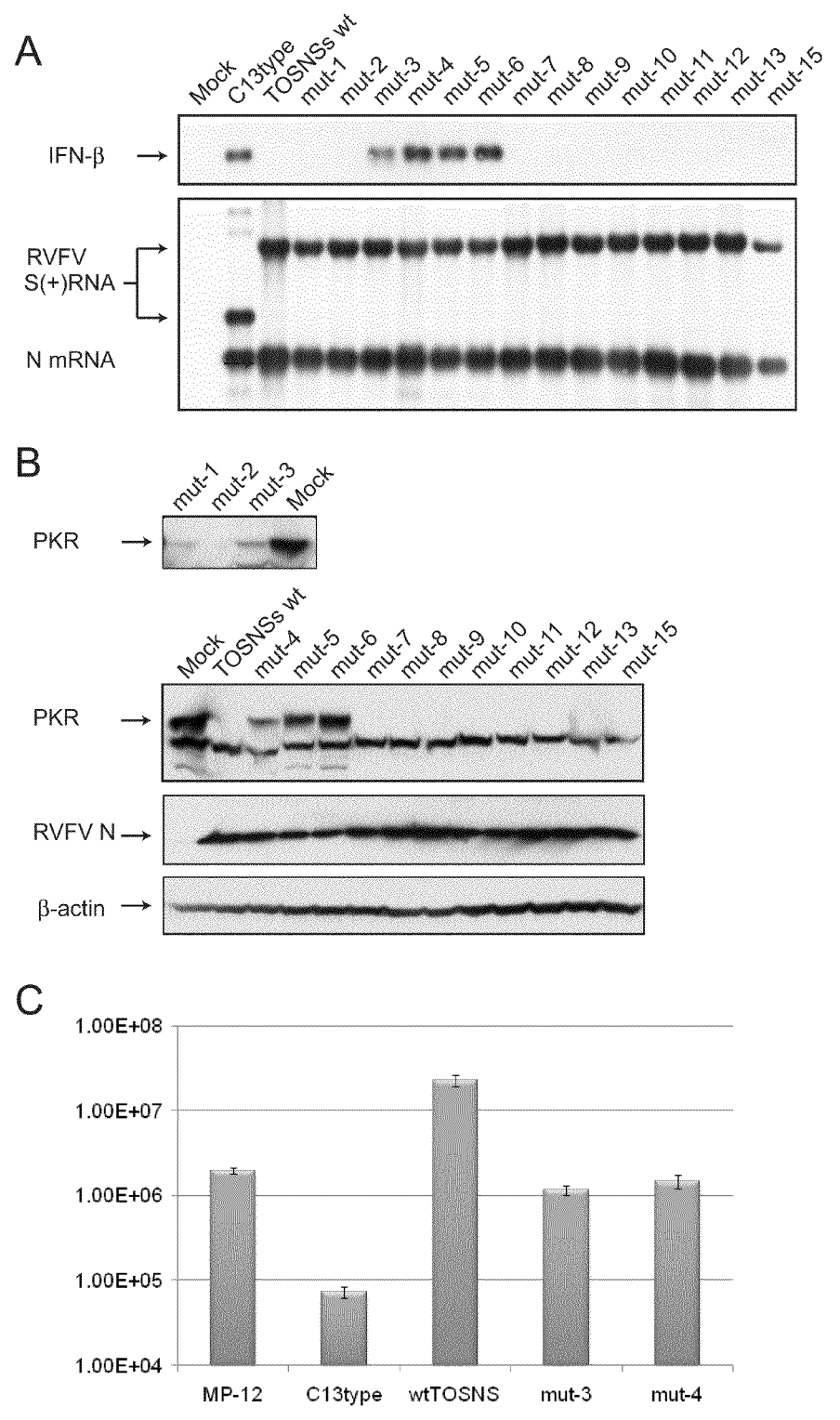

Generation and Characterization of Recombinant MP-12 Encoding Toscana Virus NSs and the Mutants (FIG. 9).

The inventor generated and characterized the recombinant MP-12 encoding Toscana virus (TOSV) NSs in place of MP-12 NSs. (A) Human lung diploid, MRC-5 cells were mock-infected or infected with rMP12-C13type (lacking NSs function), rMP12-TOSVNSs, or rMP12-TOSVNSsmut-1~15 (mut-1~15) at moi of 3. Total RNA was collected and the accumulation of IFN-b and anti-viral-sense S RNA as well as N mRNA were analyzed by Northern blot. Cells infected with C13type or mut-3, 4, 5, 6 accumulated IFN-b mRNA, while the other mutants inhibited IFN-b up-regulation upon viral infection. (B) Wild-type mouse embryonic fibroblast (MEF) cells were mock-infected or infected with rMP12-TOSVNSs or mut-1~15 at moi of 3. Accumulation of PKR, RVFV N or b-actin were analyzed by Western blot. Cells infected with mut-1, 3 or 4 induced partial degradation of PKR, whereas those infected with mut-5 or 6 failed to degrade PKR. Therefore, inventor concluded that the mut-3 and mut-4 have an ability to degrade PKR, yet lack the IFN-b suppression function. (C) Wild-type MEF cells were infected with MP-12, C13type (lacking NSs function), rMP12-TOSVNSs, mut-3 or mut-4 at moi of 0.01. Virus titers at 72 hpi were determined by plaque assay. Both mut-3 and mut-4 could efficiently replicated in type-I IFN-competent cells even though they could induce type-I IFN. mut-3: rMP12-TOSNS-K180A/H181A, mut-4: rMP12-TOSNS-H16A/K17A/R18A.

B. Materials and Methods

Media, Cells and Viruses.

Mouse embryonic fibroblast (MEF) cells (kindly provided by Dr. Bryan R. G. Williams at Monash University) were maintained in Dulbecco's modified minimum essential medium (DMEM) containing 10% fetal calf serum (FCS). BHK/T7-9 cells which express T7 RNA polymerase (Ito et al. (2003) *Microbiol Immunol* 47: 613-617) were grown in MEM-alpha containing 10% FCS. Penicillin (100 U/ml) and streptomycin (100 μg/ml) were added to the media. BHK/T7-9 cells were selected in medium containing 600 μg/ml hygromycin. MP-12 viral stock has been passaged twice in VeroE6 cells. The rMP12-C13type, which encodes NSs gene with a 69% truncation (Ikegami et al (2006) *J Virol* 80: 2933-2940) was described previously. The rMP12-NSsR173A (R173A) encodes NSs with an alanine substitution at aa.173, and does not degrade PKR in infected cells although the virus still induces host transcription suppression including IFN-β mRNA synthesis. The rMP12-mPKRN167 (N167) encodes the N-terminus of mouse PKR at aa.1 to 167 with a Flag tag in place of MP-12 NSs. Those recombinant MP-12 were recovered from BHK/T7-9 cells as described previously (Ikegami et al (2006) *J Virol* 80: 2933-2940), and passaged once in VeroE6 cells. Viral titers were determined by plaque assay in VeroE6 cells.

Plasmid.

To make a PCR fragment encoding NSs ORF of R173A, recombination PCR with the following PCR fragments were performed with KpnvNSF and XhovNSR; (1) HpavNSF: AGTTGTTAACATGGATTACTTTCCTGT-GATATCTGTTGATTTGCAG (SEQ ID NO:12) and 173AR: GGTCAATCCCTGCGAGGATGGCCTCAG (SEQ ID NO:13), (2) 173AF: CTGAGGCCATCCTCGCAGGGAT-TGACC (SEQ ID NO:14) and SpevNSR: CGCTAC-TAGTCTAATCAACCTCAACAAATCCATC (SEQ ID NO:15). The PCR fragment encoding NSs of R173A was digested with HpaI and SpeI, and inserted into the NSs ORF of pProT7-vS(+) cut with HpaI and SpeI as described previously (Ikegami et al (2006) *J Virol* 80: 2933-2940). The resulting plasmid was designated as pProT7-S(+)-NSsR173A. The N-terminus of mouse PKR (aa.1-167) with a Flag-tag at the N-terminus was amplified by PCR from first stranded cDNA derived from total RNA of wt MEF cells infected with C13type (7 hpi) with HpaFlagmPKR-F: TGTCGTTAA-CATGGATTACAAGGATGACGACGATAAGATGGC CAGTGATACCCCAGGT (SEQ ID NO:16) and Spe-m167-PKR-R: AGGAACTAGTTCAAGTTTTCG-GCGGGCTCTTTAACA (SEQ ID NO:17). Then, the PCR fragments cut with HpaI and SpeI were cloned into the NSs ORF of pProT7-vS(+) cut with HpaI and SpeI as described previously (Ikegami et al (2006) *J Virol* 80: 2933-2940). The resulting plasmid was designated as pProT7-S(+)-N167.

RNA Probes.

To generate the RNA probes to detect mouse IFN-β mRNA or mouse ISG56 mRNA, part of mouse IFN-β or mouse ISG56 was cloned between KpnI and HindIII of PSPT18 plasmid after amplification of PCR fragments from first stranded cDNA from wild-type MEF cells infected with rMP12-C13type (7 hpi). The primers used for PCR amplification of mouse IFN-β or mouse ISG56 are as follows; Kpn-mIFNb-F: GAAGGGTACCGCTCGGACCACCATCCAG-GCGTAG (SEQ ID NO:18), HindmIFNb-R: GGCTAAGCTTATGAACAACAGGTGGATC-CTCCACGC (SEQ ID NO:19), KpnmISG56F: GGGTGG-TACCGCTCCACTTTCAGAGCCTTCGCAAAGCAG (SEQ ID NO:20), HindmISG56R: TACAAAGCTTATGG-GAGAGAATGCTGATGGTGACCAGG (SEQ ID NO:21).

Recovery of Recombinant MP-12.

The R173A and N167 viruses were recovered by using a plasmid combination of pProT7-S(+)-NSsR173A, pProT7-M(+), pProT7-L(+), pT7-IRES-vN and pT7-IRES-vL, and that of pProT7-S(+)-N167, pProT7-M(+), pProT7-L(+), pT7-IRES-vN and pT7-IRES-vL, respectively, in BHK/T7-9 cells, as described previously.

Northern Blot Analysis.

RNA was extracted from purified viruses using TRIzol Reagent. Denatured RNA were separated on 1% denaturing agarose-formaldehyde gels and transferred onto a nylon membrane (Roche Applied Science). Northern blot analysis was performed as described previously with strand-specific RNA probes to detect RVFV anti-sense S-segment/N mRNA, mouse IFN-β mRNA, or mouse ISG56 mRNA (Ikegami et al. (2009) PLoS Pathog 5: e1000287; Ikegami et al. (2005) *J Virol* 79: 12106-12111).

Western Blot Analysis.

Western blot analysis was performed as described previously (Ikegami et al. (2009) PLoS Pathog 5: e1000287). The membranes were incubated with anti-PKR antibody (B-10, Santa Cruz Biotech.), anti-eIF2-alpha antibody (Cell Signaling Tech.), anti-phospho-eIF2-alpha (ser51) antibody (Cell Signaling Tech.), anti-RVFV mouse polyclonal antibody (a kind gift from Dr. R. B. Tesh, UTMB), anti-DYKDDDDK tag antibody (Cell Signaling Tech.) or anti-actin goat polyclonal antibody (I-19; Santa Cruz Biotech.) overnight at 4° C., and with secondary antibodies for 1 hr at room temperature.

Analysis of Viral Growth.

MEF cells were infected with viruses at a multiplicity of infection (moi) of 0.01 at 37° C. for 1 hr. Culture supernatants were harvested at 72 hpi, and the virus titer was measured by plaque assay. The growth curves were shown as mean+/− standard deviation from three independent experiments.

Analysis of Host Protein Synthesis.

MEF cells were infected with viruses at a moi of 3 at 37° C. for 60 min. At 16.5 h pi, cells were incubated in MEM containing 1% dialyzed FBS and 4 mM L-glutamine for 30 min, and then incubated in medium containing 100 μCi/ml of $^{35}$[S]methionine for 30 min. Cell lysates were separated by 10% polyacrylamide gel electrophoresis, and analyzed by autoradiography. The same lysates were also analyzed by coomasie blue staining to compare the amounts of loaded proteins.

Analysis of General Transcription.

MEF cells were mock-infected or infected with MP-12, C13type, R173A, or N167 at an moi of 3. At 16 hpi, 1 mM 5-ethynyluridine (EU) was added directly into cell culture, and cells were incubated for 1 hour. As a control, cells were treated with 5 μg/ml of ActD to inhibit cellular RNA synthesis for 1 hour with 1 mM EU (Ikegami et al. (2009) PLoS Pathog 5: e1000287). Cells were washed with PBS, and fixed with 125 mM Pipes pH6.8, 10 mM EGTA, 1 mM magnesium chloride, 0.2% Triton X-100 and 3.7% formaldehyde for 30 min at room temperature. After rinsing with TBS once, cells were stained at room temperature for 30 min with 100 mM Tris pH8.5, 1 mM CuSO4, 10 μM Alexa Fluor 594-coupled azide (Invitrogen), and 100 mM ascorbic acid. The addition of ascorbic acid will reduce copper (II), and produce copper (I) in situ, where a copper catalyzes covalent reaction between a fluorescent azide and an alkyne of EU (click reaction)(Jao and Salic (2008) *Proc Natl Acad Sci USA* 105: 15779-15784. After staining, cells were washed 4 times with TBS containing 0.5% Triton X-100, then reacted with anti-RVFV antibody, following by the staining with Alexa Fluor 488-conjugated anti-mouse IgG, and DAPI. Cells were imaged with fluorescent microscopy to detect cellular RNA that incorporated EU in 1 hour. Fluorescence-activated cell sorting (FACS) analysis were performed in 293 cells. 293 cells were mock-infected or infected with MP-12, C13type or R173A at moi of 3, and treated with 0.5 mM EU at 8 hpi for 1 hour. The control cells were co-treated with ActD (5 μg/ml) at 8 hpi for 1 hour. Incorporated EU was stained with Alexa Fluor 647-azide, and viral antigens were stained with anti-RVFV antibodies. Cells were then analyzed by flow cytometry on the LSRII Fortessa.

Mouse Experiment.

For testing humoral immune responses 5-week-old female CD1 outbred mice were inoculated subcutaneously with PBS (mock) (n=5), or $1\times10^5$ pfu of MP-12 (n=10), C13type (n=10), R173A (n=10) or N167 (n=10). At 1, 2, 3, 30, 90 and 180 dpi, less than 100 μl of blood were collected from retro-orbital vein, and serum samples were obtained for IFN-α ELISA, virus plaque assay and $PRNT_{80}$. For testing efficacy of MP-12 NSs mutants, 5-week-old female CD1 outbred mice were inoculated subcutaneously with PBS (mock) (n=10), or $1\times10^5$ pfu of MP-12 (n=11), C13type (n=10), R173A (n=10), or N167 (n=9). Sera were collected at 42 dpi, and mice were challenged with $1\times10^3$ pfu of wt RVFV ZH501 strain (i.p) at 44 dpi. The challenge experiment was performed at animal biosafety level 4 facility at UTMB. Mice were observed for 21 days and the body weight was monitored daily. For testing viral antigen accumulation at draining lymph nodes, 5-week-old female CD1 outbred mice were inoculated at footpad (30 μl) with PBS (mock) (n=3), or $1\times10^5$ pfu of MP-12 (n=4), C13type (n=4), R173A (n=4), N167 (n=4) or heat-inactivated MP-12 (n=3). The draining lymph nodes (popliteal and inguinal) were collected at 1 dpi, and used for antigen capture ELISA. Mice immunized with MP-12 (n=3) or R173A (n=3) were also tested at 2 and 3 dpi. For testing cytokines and chemokines in mouse sera, 5-week-old female CD1 outbred mice were inoculated at footpad (30 μl) with PBS (mock) (n=3), or $1\times10^5$ pfu of MP-12 (n=4), C13type (n=4), R173A (n=4), or N167 (n=4). Sera were collected at 2 dpi, and used for Bio-Plex analysis.

Detection of Cytokines and Chemokines in Mouse Sera.

Cytokines and chemokines in mouse sera collected at 2 dpi were measured by Bio-Plex Pro Mouse Cytokine 23-Plex Assay (BioRad) according to manufacturer's instructions. Cytokine reference standards (2 to 32,000 μg/ml) provided by the manufacturer were included in the assay. Mouse sera (15 μl) and universal sample diluents in the kit (45 ml) were mixed and loaded onto 96-well plate containing beads (each 50 μl). The raw data were statistically compared by two-way ANOVA first, and the fold difference from mock-infected samples was analyzed subsequently.

Antigen-Capture ELISA.

Popliteal and inguinal lymph nodes were separately collected into tube containing 120 ml of PBS with 1% Triton X-100, 0.05% Tween 20 and 1% skim milk on ice. After homogenization, samples were centrifuged at 15,000 g at 4° C. for 5 min. Then, 100 μl of lysate sample was used for ELISA. 96-well flat-bottom plate was coated with 125 ng of monoclonal antibody (D5-59) against RVFV N in PBS overnight at 4° C. After washing 3 times with PBS with 0.05% Tween 20 (PBS-T), wells were blocked with PBS-T containing 5% skim milk for 2 hours at room temperature. Subsequently, lymph node lysates were added into well, and incubated at 37° C. for 1 hour. Plate was washed with PBS-T for 3 times, and rabbit anti-RVFV serum (1:1000) was added as detection antibody, and incubated at 37° C. for 1 hour. After washing with PBS-T for 3 times, wells were reacted with HRP-labeled anti-rabbit IgG at 37° C. for 1 hour. After washing with PBS-T for 3 times, 2,2'-azinobis[3-ethylbenziazoline-6-sulfonic acid] (ABTS) substrate (ABTS tablet and buffer; Roche Diagnostics) was added to wells. The plate was incubated at room temperature for 30 min, and the optical density at 415 nm was recorded.

IgG-ELISA.

RVFV N proteins were expressed and purified by using baculovirus vector according to manufacturer's instruction. N proteins were tagged with 6×His tag, and purified with Ni-NTA HisBind Superflow Resin (EMD4BioSciences) according to the manufacturer's instruction. 96-well flat-bottom plate was coated with 50 ng of RVFV N for overnight at 4° C. After washing 3 times with PBS-T, wells were blocked with PBS-T containing 5% skim milk at 37° C. for 2 hours. Then, wells were incubated with serum samples with 2-fold serial dilutions at 37° C. for 1 hour. Wells were washed for 3 times with PBS-T, and reacted with HRP-conjugated anti-mouse IgG (Santa Cruz Technologies) at 37° C. for 1 hour. After washing with PBS-T for 3 times, ABTS was added to wells. The plate was incubated at room temperature for 30 min, and the optical density at 415 nm was recorded. The cut-off value of IgG-ELISA (OD 415 nm of 0.36) was defined as mean+2× standard deviation of 36 normal mouse sera (1:400) in this study. The highest dilution of sera that makes larger OD value than cut-off was designated as anti-N antibody titer.

Plaque Reduction Neutralization Test.

Mouse sera (6 μl) and DMEM containing 10% FBS (42 μl) were mixed, and serially 4-fold diluted subsequently. Each 20 μl of diluents was transferred into flat-bottom 96-well plate containing 5 μl of MP-12 virus (50 pfu/well) (final dilutions of sera: 1:10, 1:40, 1:160~). Plate was incubated at 37° C. for 1 hour, and 150 μl of DMEM with 10% FBS was added to well. The 150 μl of mixture was transferred into 24-well plate with confluent VeroE6 cells, and the plate was incubated at 37° C. for 1 hour. After removal of inocula, 0.5 ml of 1:1 mixture of 1.2% noble agar in water and 2×MEM (Gibco) was overlaid to each well. At 2 dpi, 0.5 ml of the second overlay containing neutral red was added into each well, and incubated overnight. The average of the plaque numbers at the well added with mock-immunized mouse sera in 6 different wells was used as cut-off number (typically 8~9). The highest dilution of sera that produced the number of plaques below the cut-off number was designated as $PRNT_{80}$ NAb titer.

The invention claimed is:

1. A Rift Valley fever virus (RVFV) S genome segment comprising a heterologous nucleic acid inserted into the NSs coding region of the RVFV, wherein the heterologous nucleic acid encodes a dominant negative dsRNA dependent protein kinase (PKR) inhibitor of SEQ ID NO:2.

2. The S genome segment of claim 1, wherein S genome segment comprises a deletion of all or substantially all of NSs gene.

3. A vector encoding the S genome segment of claim 1.

4. An isolated cell expressing the genome segment of claim 1.

5. An attenuated virus comprising the S genome segment of claim 1.

6. The attenuated virus of claim 5, wherein the Rift Valley fever virus is a MP-12 Rift Valley fever virus.

7. An immunogenic composition comprising the attenuated virus of claim 5.

8. The composition of claim 7, further comprising an adjuvant.

9. A kit comprising an S genome segment of claim 1, a virus of claim 5, or an immunogenic composition of claim 6.

\* \* \* \* \*

SEQUENCE LISTING

<160> NUMBER OF SEQ ID NOS: 21

<210> SEQ ID NO 1
<211> LENGTH: 515
<212> TYPE: PRT
<213> ORGANISM: Mus musculus

<400> SEQUENCE: 1

Met Ala Ser Asp Thr Pro Gly Phe Tyr Met Asp Lys Leu Asn Lys Tyr
1               5                   10                  15

Arg Gln Met His Gly Val Ala Ile Thr Tyr Lys Glu Leu Ser Thr Ser
            20                  25                  30

Gly Pro Pro His Asp Arg Arg Phe Thr Phe Gln Val Leu Ile Asp Glu
        35                  40                  45

Lys Glu Phe Pro Glu Ala Lys Gly Arg Ser Lys Gln Glu Ala Arg Asn
    50                  55                  60

Ala Ala Ala Lys Leu Ala Val Asp Ile Leu Asp Asn Glu Asn Lys Val
65                  70                  75                  80

Asp Cys His Thr Ser Ala Ser Glu Gln Gly Leu Phe Val Gly Asn Tyr
                85                  90                  95

Ile Gly Leu Val Asn Ser Phe Ala Gln Lys Lys Leu Ser Val Asn
            100                 105                 110

Tyr Glu Gln Cys Glu Pro Asn Ser Glu Leu Pro Gln Arg Phe Ile Cys
            115                 120                 125

Lys Cys Lys Ile Gly Gln Thr Met Tyr Gly Thr Gly Ser Gly Val Thr
130                 135                 140

Lys Gln Glu Ala Lys Gln Leu Ala Ala Lys Glu Ala Tyr Gln Lys Leu
145                 150                 155                 160

Leu Lys Ser Pro Pro Lys Thr Ala Gly Thr Ser Ser Val Val Thr
            165                 170                 175

Ser Thr Phe Ser Gly Phe Ser Ser Ser Ser Met Thr Ser Asn Gly
            180                 185                 190

Val Ser Gln Ser Ala Pro Gly Ser Phe Ser Ser Glu Asn Val Phe Thr
            195                 200                 205

Asn Gly Leu Gly Glu Asn Lys Arg Lys Ser Gly Val Lys Val Ser Pro
    210                 215                 220

Asp Asp Val Gln Arg Asn Lys Tyr Thr Leu Asp Ala Arg Phe Asn Ser
225                 230                 235                 240

Asp Phe Glu Asp Ile Glu Glu Ile Gly Leu Gly Gly Phe Gly Gln Val
            245                 250                 255

Phe Lys Ala Lys His Arg Ile Asp Gly Lys Arg Tyr Ala Ile Lys Arg
            260                 265                 270

Val Lys Tyr Asn Thr Glu Lys Ala Glu His Glu Val Gln Ala Leu Ala
            275                 280                 285

Glu Leu Asn His Val Asn Ile Val Gln Tyr His Ser Cys Trp Glu Gly
            290                 295                 300

Val Asp Tyr Asp Pro Glu His Ser Met Ser Asp Thr Ser Arg Tyr Lys
305                 310                 315                 320

Thr Arg Cys Leu Phe Ile Gln Met Glu Phe Cys Asp Lys Gly Thr Leu
            325                 330                 335

Glu Gln Trp Met Arg Asn Arg Asn Gln Ser Lys Val Asp Lys Ala Leu
            340                 345                 350

Ile Leu Asp Leu Tyr Glu Gln Ile Val Thr Gly Val Gly Tyr Ile His
            355                 360                 365

```
Ser Lys Gly Leu Ile His Arg Asp Leu Lys Pro Gly Asn Ile Phe Leu
    370                 375                 380
Val Asp Glu Arg His Ile Lys Ile Gly Asp Phe Gly Leu Ala Thr Ala
385                 390                 395                 400
Leu Glu Asn Asp Gly Lys Ser Arg Thr Arg Arg Thr Gly Thr Leu Gln
                405                 410                 415
Tyr Met Ser Pro Glu Gln Leu Phe Leu Lys His Tyr Gly Lys Glu Val
            420                 425                 430
Asp Ile Phe Ala Leu Gly Leu Ile Leu Ala Glu Leu Leu His Thr Cys
        435                 440                 445
Phe Thr Glu Ser Glu Lys Ile Lys Phe Phe Glu Ser Leu Arg Lys Gly
    450                 455                 460
Asp Phe Ser Asn Asp Ile Phe Asp Asn Lys Glu Lys Ser Leu Leu Lys
465                 470                 475                 480
Lys Leu Leu Ser Glu Lys Pro Lys Asp Arg Pro Glu Thr Ser Glu Ile
                485                 490                 495
Leu Lys Thr Leu Ala Glu Trp Arg Asn Ile Ser Glu Lys Lys Lys Arg
            500                 505                 510
Asn Thr Cys
        515

<210> SEQ ID NO 2
<211> LENGTH: 167
<212> TYPE: PRT
<213> ORGANISM: Artificial Sequence
<220> FEATURE:
<223> OTHER INFORMATION: Recombinant protein

<400> SEQUENCE: 2

Met Ala Ser Asp Thr Pro Gly Phe Tyr Met Asp Lys Leu Asn Lys Tyr
1               5                   10                  15
Arg Gln Met His Gly Val Ala Ile Thr Tyr Lys Glu Leu Ser Thr Ser
            20                  25                  30
Gly Pro Pro His Asp Arg Arg Phe Thr Phe Gln Val Leu Ile Asp Glu
        35                  40                  45
Lys Glu Phe Pro Glu Ala Lys Gly Arg Ser Lys Gln Glu Ala Arg Asn
    50                  55                  60
Ala Ala Ala Lys Leu Ala Val Asp Ile Leu Asp Asn Glu Asn Lys Val
65                  70                  75                  80
Asp Cys His Thr Ser Ala Ser Glu Gln Gly Leu Phe Val Gly Asn Tyr
                85                  90                  95
Ile Gly Leu Val Asn Ser Phe Ala Gln Lys Lys Lys Leu Ser Val Asn
            100                 105                 110
Tyr Glu Gln Cys Glu Pro Asn Ser Glu Leu Pro Gln Arg Phe Ile Cys
        115                 120                 125
Lys Cys Lys Ile Gly Gln Thr Met Tyr Gly Thr Gly Ser Gly Val Thr
    130                 135                 140
Lys Gln Glu Ala Lys Gln Leu Ala Ala Lys Glu Ala Tyr Gln Lys Leu
145                 150                 155                 160
Leu Lys Ser Pro Pro Lys Thr
                165

<210> SEQ ID NO 3
<211> LENGTH: 551
<212> TYPE: PRT
<213> ORGANISM: Homo sapiens
```

```
<400> SEQUENCE: 3

Met Ala Gly Asp Leu Ser Ala Gly Phe Phe Met Glu Glu Leu Asn Thr
  1               5                  10                  15

Tyr Arg Gln Lys Gln Gly Val Val Leu Lys Tyr Gln Glu Leu Pro Asn
             20                  25                  30

Ser Gly Pro Pro His Asp Arg Arg Phe Thr Phe Gln Val Ile Ile Asp
         35                  40                  45

Gly Arg Glu Phe Pro Glu Gly Glu Gly Arg Ser Lys Lys Glu Ala Lys
     50                  55                  60

Asn Ala Ala Ala Lys Leu Ala Val Glu Ile Leu Asn Lys Glu Lys Lys
 65                  70                  75                  80

Ala Val Ser Pro Leu Leu Leu Thr Thr Thr Asn Ser Ser Glu Gly Leu
                 85                  90                  95

Ser Met Gly Asn Tyr Ile Gly Leu Ile Asn Arg Ile Ala Gln Lys Lys
                100                 105                 110

Arg Leu Thr Val Asn Tyr Glu Gln Cys Ala Ser Gly Val His Gly Pro
            115                 120                 125

Glu Gly Phe His Tyr Lys Cys Lys Met Gly Gln Lys Glu Tyr Ser Ile
        130                 135                 140

Gly Thr Gly Ser Thr Lys Gln Glu Ala Lys Gln Leu Ala Ala Lys Leu
145                 150                 155                 160

Ala Tyr Leu Gln Ile Leu Ser Glu Glu Thr Ser Val Lys Ser Asp Tyr
                165                 170                 175

Leu Ser Ser Gly Ser Phe Ala Thr Thr Cys Glu Ser Gln Ser Asn Ser
            180                 185                 190

Leu Val Thr Ser Thr Leu Ala Ser Glu Ser Ser Glu Gly Asp Phe
        195                 200                 205

Ser Ala Asp Thr Ser Glu Ile Asn Ser Asn Ser Asp Ser Leu Asn Ser
    210                 215                 220

Ser Ser Leu Leu Met Asn Gly Leu Arg Asn Asn Gln Arg Lys Ala Lys
225                 230                 235                 240

Arg Ser Leu Ala Pro Arg Phe Asp Leu Pro Asp Met Lys Glu Thr Lys
                245                 250                 255

Tyr Thr Val Asp Lys Arg Phe Gly Met Asp Phe Lys Glu Ile Glu Leu
                260                 265                 270

Ile Gly Ser Gly Gly Phe Gly Gln Val Phe Lys Ala Lys His Arg Ile
            275                 280                 285

Asp Gly Lys Thr Tyr Val Ile Lys Arg Val Lys Tyr Asn Asn Glu Lys
        290                 295                 300

Ala Glu Arg Glu Val Lys Ala Leu Ala Lys Leu Asp His Val Asn Ile
305                 310                 315                 320

Val His Tyr Asn Gly Cys Trp Asp Gly Phe Asp Tyr Asp Pro Glu Thr
                325                 330                 335

Ser Asp Asp Ser Leu Glu Ser Ser Asp Tyr Asp Pro Glu Asn Ser Lys
            340                 345                 350

Asn Ser Ser Arg Ser Lys Thr Lys Cys Leu Phe Ile Gln Met Glu Phe
        355                 360                 365

Cys Asp Lys Gly Thr Leu Glu Gln Trp Ile Glu Lys Arg Arg Gly Glu
    370                 375                 380

Lys Leu Asp Lys Val Leu Ala Leu Glu Leu Phe Glu Gln Ile Thr Lys
385                 390                 395                 400

Gly Val Asp Tyr Ile His Ser Lys Lys Leu Ile His Arg Asp Leu Lys
                405                 410                 415
```

```
Pro Ser Asn Ile Phe Leu Val Asp Thr Lys Gln Val Lys Ile Gly Asp
            420                 425                 430
Phe Gly Leu Val Thr Ser Leu Lys Asn Asp Gly Lys Arg Thr Arg Ser
        435                 440                 445
Lys Gly Thr Leu Arg Tyr Met Ser Pro Glu Gln Ile Ser Ser Gln Asp
    450                 455                 460
Tyr Gly Lys Glu Val Asp Leu Tyr Ala Leu Gly Leu Ile Leu Ala Glu
465                 470                 475                 480
Leu Leu His Val Cys Asp Thr Ala Phe Glu Thr Ser Lys Phe Phe Thr
                485                 490                 495
Asp Leu Arg Asp Gly Ile Ile Ser Asp Ile Phe Asp Lys Lys Glu Lys
            500                 505                 510
Thr Leu Leu Gln Lys Leu Leu Ser Lys Lys Pro Glu Asp Arg Pro Asn
        515                 520                 525
Thr Ser Glu Ile Leu Arg Thr Leu Thr Val Trp Lys Lys Ser Pro Glu
    530                 535                 540
Lys Asn Glu Arg His Thr Cys
545                 550

<210> SEQ ID NO 4
<211> LENGTH: 1690
<212> TYPE: DNA
<213> ORGANISM: Rift Valley fever virus

<400> SEQUENCE: 4
acacaaagct ccctagagat acaaacacta ttacaataat ggacaactat caagagcttg    60
cgatccagtt tgctgctcaa gcagtggacc gcaatgagat tgaacagtgg gtccgagagt   120
ttgcttatca agggtttgat gcccgtagag ttatcgaact cttaaagcag tatggtgggg   180
ctgactggga gaaggatgcc aagaaaatga ttgttctggc tctaactcgt ggcaacaagc   240
ccaggaggat gatgataaaa atgtcgaaag aaggcaaagc aactgtggag ctctcatca    300
acaagtataa gctaaaggaa gggaatcctt cccgggatga gttgactcta tcacgagttg   360
ctgccgccct ggctggctgg acatgccagg cttttggtcgt cttgagtgag tggcttcctg   420
tcactgggac taccatggac ggcctatccc ctgcataccc gaggcatatg atgcacccca   480
gctttgctgg catggtggat ccttctctac caggagacta tctaagggca atattagatg   540
ctcactctct gtatctgctg cagttctccc gggtcatcaa cccaaacctc gaggtagaa    600
caaaagagga ggttgctgca cgttcacgc agccaatgaa tgcagcagtg aatagcaact   660
ttataagcca tgagaagagg agagaattct tgaaagcctt tggacttgtg gattccaatg   720
ggaagccgtc agctgctgtc atggcagccg ctcaggctta caagacagca gcctaagtgg   780
ctgcccaggg ggttgggggg aagggagtt ggggttacgg tcgggattag ggggtggggg    840
gtggggcagc cttaacctct aatcaacctc aacaaatcca tcatcatcac tctcctcctc   900
tgattccatc tcaacatctg ggattggagg aataactgga atccagttgt ttctccccat   960
catgctggga agtgatgagc gcagcatcag gctctcctcc ataagaacaa tgagggctga  1020
gtttggaact acagcattag aaatgtcctc ttttgctgct tgcagaagcc gaacgcactg  1080
tacgtgagca acctcataca tgagatcaaa gcctggcaac aggcacaggt caatccctct  1140
gaggatggcc tcagtcgcta tcatcctgtg taagccagca aaggagtcct ctagatcatt  1200
ggtgatcttg caactcctca ttgctagagt ggcaatctga tcccttctaa tgtcatcatt  1260
cctatgcact ctagtagagc ttaggtcgaa gaaagccagt gagggttctc caagaggcca  1320
```

```
ggatatggct tctttcagat tggggaacct tgtgaaatca ctaagagtca tatggcctat    1380
tagatcaata agtctctgaa aaggcttcgc tggtggaggt gcaacgtttg atgcaaagtc    1440
tccaagtccg actcggtatg ggaattctcc gacattgtag aagtcagaga tcgcaagcg     1500 aacctcgtga ctaggacgat ggtgcatgag aaagacacaa cagggcccaa ccatagaata    1560
aggtatcctg gaggaccat ctcctctaaa gtactccact gacacaacac gacgaccact     1620
ctgcaaatca acagatatca caggaaagta atccatgata tacttgataa gcactagggg    1680
gtctttgtgt                                                           1690

<210> SEQ ID NO 5
<211> LENGTH: 1442
<212> TYPE: DNA
<213> ORGANISM: Artificial Sequence
<220> FEATURE:
<223> OTHER INFORMATION: Recombinant DNA

<400> SEQUENCE: 5
acacaaagct ccctagagat acaaacacta ttacaataat ggacaactat caagagcttg      60
cgatccagtt tgctgctcaa gcagtggacc gcaatgagat tgaacagtgg gtccgagagt     120
ttgcttatca agggtttgat gcccgtagag ttatcgaact cttaaagcag tatggtgggg     180
ctgactggga aaggatgcc aagaaaatga ttgttctggc tctaactcgt ggcaacaagc      240
ccaggaggat gatgatgaaa atgtcgaaag aaggcaaagc aactgtggag gctctcatca     300
acaagtataa gctaaaggaa gggaatcctt cccgggatga gttgactcta tcacgagttg     360
ctgccgcctt ggctggctgg acatgccagg cttttggtcgt cttgagtgag tggcttcctg     420
tcactgggac taccatggac ggcctatccc ctgcataccc gaggcatatg atgcacccca     480
gctttgctgg catggtggat ccttctctac caggagacta tctaagggca atattagatg     540
ctcactctct gtatctgctg cagttctccc gggtcatcaa cccaaacctc cgaggtagaa     600
caaaagagga ggttgctgca acgttcacgc agccaatgaa tgcagcagtg aatagcaact     660
ttataagcca tgagaagagg agagaattct tgaaagcctt tggacttgtg gattccaatg     720
ggaagccgtc agctgctgtc atggcagccg ctcaggctta caagacagca gcctaagtgg     780
ctgcccaggg ggttgggggg aaggggagtt ggggttacgg tcgggattag ggggtggggg     840
gtggggcagc cttaacctct aatcaacctc aactagttca gttttcggc gggctctttta     900 acagcttctg ataggcttct ttcgcagcca actgctttgc ctcctgtttg gtgacacctg     960
aaccagtacc atacattgtc tgcccaattt tgcatttaca aataaatctt tgaggcaact    1020
cagagttggg ctcacactgt tcataattta cagacagctt tttcttctgg gcaaagctat    1080
tgacaaggcc tatgtagtta ccaacgaaca agccttgctc agatgcactc gtgtgacaat    1140
ccaccttgtt ttcgttatca agtatatcaa cagctaattt ggctgcagcg tttcttgcct    1200
cctgctttga tctaccttta gcttctggaa attccttctc atctattaaa acttgaaatg    1260
taaaccttct gtcatgtgga ggtcccgaag tactaagttc tttatacgta atggctactc    1320
cgtgcatctg gcggtattta ttaagtttgt ccatgtagaa acctgggggta tcactggcca    1380 tcttatcgtc gtcatccttg taatccatgt taaccttgat aagcactagg gggtctttgt    1440
gt                                                                   1442

<210> SEQ ID NO 6
<211> LENGTH: 1442
<212> TYPE: DNA
```

<213> ORGANISM: Rift Valley fever virus

<400> SEQUENCE: 6

```
acacaaagct ccctagagat acaaacacta ttacaataat ggacaactat caagagcttg    60
cgatccagtt tgctgctcaa gcagtggacc gcaatgagat tgaacagtgg gtccgagagt   120
ttgcttatca agggtttgat gcccgtagag ttatcgaact cttaaagcag tatggtgggg   180
ctgactggga gaaggatgcc aagaaaatga ttgttctggc tctaactcgt ggcaacaagc   240
ccaggaggat gatgatgaaa atgtcgaaag aaggcaaagc aactgtggag gctctcatca   300
acaagtataa gctaaaggaa gggaatcctt cccgggatga gttgactcta tcacgagttg   360
ctgccgcctt ggctggctgg acatgccagg ctttggtcgt cttgagtgag tggcttcctg   420
tcactgggac taccatggac ggcctatccc ctgcataccc gaggcatatg atgcacccca   480
gctttgctgg catggtggat ccttctctac caggagacta tctaagggca atattagatg   540
ctcactctct gtatctgctg cagttctccc gggtcatcaa cccaaacctc cgaggtagaa   600
caaaagagga ggttgctgca cgttcacgc agccaatgaa tgcagcagtg aatagcaact   660
ttataagcca tgagaagagg agagaattct tgaaagcctt tggacttgtg gattccaatg   720
ggaagccgtc agctgctgtc atggcagccg ctcaggctta caagacagca gcctaagtgg   780
ctgcccaggg ggttgggggg aaggggagtt ggggttacgg tcgggattag ggggtggggg   840
gtggggcagc cttaacctct aatcaacctc aactagttca agtttcggc gggctcttta   900
acagcttctg ataggcttct ttcgcagcca actgctttgc ctcctgtttg gtgacacctg   960
aaccagtacc atacattgtc tgcccaattt tgcatttaca aataaatctt tgaggcaact  1020
cagagttggg ctcacactgt tcataattta cagacagctt tttcttctgg gcaaagctat  1080
tgacaaggcc tatgtagtta ccaacgaaca agccttgctc agatgcactc gtgtgacaat  1140
ccaccttgtt ttcgttatca agtatatcaa cagctaattt ggctgcagcg tttcttgcct  1200
cctgctttga tctaccttg gcttctggaa attccttctc atctattaaa acttgaaatg  1260
taaaccttct gtcatgtgga ggtcccgaag tactaagttc tttatacgta atggctactc  1320
cgtgcatctg gcggtattta ttaagtttgt ccatgtagaa acctgggta tcactggcca  1380
tcttatcgtc gtcatccttg taatccatgt taaccttgat aagcactagg gggtctttgt  1440
gt                                                                 1442
```

<210> SEQ ID NO 7
<211> LENGTH: 951
<212> TYPE: DNA
<213> ORGANISM: Rift Valley fever virus

<400> SEQUENCE: 7

```
atgcaatcca gagctgtcat cttgaagtat agatctggtt caggccacaa gaggtctttg    60
cccaggttct acatagactg tgatttggac acctttgatt ttgagaagga ttgctctctg   120
attgagaatg agttccccat ttacataaac aattataagg tggtctataa gtcaaagcca   180
actctctcac atttcctcat tgagaaggag tttcctgctg tgctggggcc tggtatgatc   240
agtgcagttc gaaccagact ttacgagcca actatgagag agctctacca ggaatcgatt   300
caccaactaa agaggagcaa caagagatac cttttgtctg ctctcaggtg gcccacaggg   360
attcctactc tagagtttat agactattac ttcgaggagc tcctgttctt gtcagagttt   420
gacccggggt ctatccagag ataccctgaa attactggtta aggcctctgg gctttacaac   480
tccactaatg aggagcagat agtggagatt cacagacgag tgctcataga aggcgcagcg   540
```

```
cacggattga ctgcttttga tctcccagga aatgacatcc ttggagacat ctgtgtggtc    600
caagcagcac gggtgacaag actggttgct aagacattct ctaagatgac cagagacacc    660
catctgatga tacttctc gataagccca gttgagttgg ttttgagtaa acttgataag     720
aaaggggaca gagggctaa agcaaaaggg ttgatgtcta tgagtgccgc taggtcttat    780
gactatttta tgagaactga cttgggattc agagagactg ctctttccac cttttgggct    840
aaggactggc ctaccccaca agagaccatt ctatctgaca aacgatgcct taaagaagac    900
atgagagtga caaagtggct gcctagtccc cccactacc caccttatg a              951
```

<210> SEQ ID NO 8
<211> LENGTH: 951
<212> TYPE: DNA
<213> ORGANISM: Rift Valley fever virus

<400> SEQUENCE: 8

```
atgcaatcca gagctgtcat cttgaagtat agatctggtt caggcgccgc ggcgtctttg     60
cccaggttct acatagactg tgatttggac acctttgatt ttgagaagga ttgctctctg    120
attgagaatg agttccccat ttacataaac aattataagg tggtctataa gtcaaagcca    180
actctctcac atttcctcat tgagaaggag tttcctgctg tgctggggcc tggtatgatc    240
agtgcagttc gaaccagact ttacgagcca actatgagag agctctacca ggaatcgatt    300
caccaactaa agaggagcaa caagagatac cttttgtctg ctctcaggtg gcccacaggg    360
attcctactc tagagtttat agactattac ttcgaggagc tcctgttctt gtcagagttt    420
gacccggggt ctatccagag atacctgaaa ttactggtta aggcctctgg ctttacaac    480 tccactaatg aggagcagat agtggagatt cacagacgag tgctcataga aggcaaaaag    540
cacggattga ctgcttttga tctcccagga aatgacatcc ttggagacat ctgtgtggtc    600
caagcagcac gggtgacaag actggttgct aagacattct ctaagatgac cagagacacc    660
catctgatga tacttctc gataagccca gttgagttgg ttttgagtaa acttgataag     720
aaaggggaca gagggctaa agcaaaaggg ttgatgtcta tgagtgccgc taggtcttat    780
gactatttta tgagaactga cttgggattc agagagactg ctctttccac cttttgggct    840
aaggactggc ctaccccaca agagaccatt ctatctgaca aacgatgcct taaagaagac    900
atgagagtga caaagtggct gcctagtccc cccactacc caccttatg a              951
```

<210> SEQ ID NO 9
<211> LENGTH: 1862
<212> TYPE: DNA
<213> ORGANISM: Rift Valley fever virus

<400> SEQUENCE: 9

```
acacaaagct ccctagagat acaaacacta ttacaataat ggacaactat caagagcttg     60
cgatccagtt tgctgctcaa gcagtggacc gcaatgagat tgaacagtgg gtccgagagt    120
ttgcttatca agggtttgat gcccgtagag ttatcgaact cttaaagcag tatggtgggg    180
ctgactggga gaaggatgcc aagaaaatga ttgttctggc tctaactcgt ggcaacaagc    240
ccaggaggat gatgatgaaa atgtcgaaag aaggcaaagc aactgtggag ctctcatca    300 acaagtataa gctaaaggaa gggaatcctt cccgggatga gttgactcta tcacgagttg    360
ctgccgcctt ggctggctgg acatgccagg ctttggtcgt cttgagtgag tggcttcctg    420
tcactgggac taccatggac ggcctatccc ctgcataccc gaggcatatg atgcacccca    480
```

```
gctttgctgg catggtggat ccttctctac caggagacta tctaagggca atattagatg    540
ctcactctct gtatctgctg cagttctccc gggtcatcaa cccaaacctc cgaggtagaa    600
caaaagagga ggttgctgca acgttcacgc agccaatgaa tgcagcagtg aatagcaact    660
ttataagcca tgagaagagg agagaattct tgaaagcctt tggacttgtg gattccaatg    720
ggaagccgtc agctgctgtc atggcagccg ctcaggctta agacagca gcctaagtgg     780
```

```
ctgcccaggg ggtgggggg aaggggagtt ggggttacgg tcgggattag ggggtggggg    840
gtggggcagc cttaacctct aatcaacctc aactagttca taagggtggg tagtgggggg    900
gactaggcag ccactttgtc actctcatgt cttctttaag gcatcgtttg tcagatagaa    960
tggtctcttg tggggtaggc cagtccttag cccaaaaggt ggaaagagca gtctctctga   1020
atcccaagtc agttctcata aaatagtcat aagacctagc ggcactcata gacatcaacc   1080
cttttgcttt agccctcttg tccccttcct tatcaagttt actcaaaacc aactcaactg   1140
ggcttatcga gaagtatatc atcagatggg tgtctctggt catcttagag aatgtcttag   1200
caaccagtct tgtcacccgt gctgcttgga ccacacagat gtctccaagg atgtcatttc   1260
ctgggagatc aaaagcagtc aatccgtgct ttttgccttc tatgagcact cgtctgtgaa   1320
tctccactat ctgctcctca ttagtggagt tgtaaagccc agaggcctta accagtaatt   1380
tcaggtatct ctggatagac cccgggtcaa actctgacaa gaacaggagc tcctcgaagt   1440
aatagtctat aaactctaga gtaggaatcc ctgtgggcca cctgagagca gacaaaaggt   1500
atctcttgtt gctcctcttt agttggtgaa tcgattcctg gtagagctct ctcatagttg   1560
gctcgtaaag tctggttcga actgcactga tcataccagg ccccagcaca gcaggaaact   1620
ccttctcaat gaggaaatgt gagagagttg gctttgactt atagaccacc ttataattgt   1680
ttatgtaaat ggggaactca ttctcaatca gagagcaatc cttctcaaaa tcaaaggtgt   1740
ccaaatcaca gtctatgtag aacctgggca aagacctctt gtggcctgaa ccagatctat   1800
acttcaagat gacagctctg gattgcatgt taaccttgat aagcactagg gggtctttgt   1860
gt                                                                  1862
```

<210> SEQ ID NO 10
<211> LENGTH: 1862
<212> TYPE: DNA
<213> ORGANISM: Rift Valley fever virus

<400> SEQUENCE: 10

```
acacaaagct ccctagagat acaaacacta ttacaataat ggacaactat caagagcttg     60
cgatccagtt tgctgctcaa gcagtggacc gcaatgagat tgaacagtgg gtccgagagt    120
ttgcttatca agggtttgat gcccgtagag ttatcgaact cttaaagcag tatggtgggg    180
ctgactggga gaaggatgcc aagaaaatga ttgttctggc tctaactcgt ggcaacaagc    240
ccaggaggat gatgatgaaa atgtcgaaag aaggcaaagc aactgtggag gctctcatca    300
acaagtataa gctaaaggaa gggaatcctt cccgggatga gttgactcta tcacgagttg    360
ctgccgcctt ggctggctgg acatgccagg cttggtcgt cttgagtgag tggcttcctg    420
tcactgggac taccatggac ggcctatccc ctgcatcccc gaggcatatg atgcacccca    480
gctttgctgg catggtggat ccttctctac caggagacta tctaagggca atattagatg    540
ctcactctct gtatctgctg cagttctccc gggtcatcaa cccaaacctc cgaggtagaa    600
caaaagagga ggttgctgca acgttcacgc agccaatgaa tgcagcagtg aatagcaact    660
ttataagcca tgagaagagg agagaattct tgaaagcctt tggacttgtg gattccaatg    720
```

-continued

```
ggaagccgtc agctgctgtc atggcagccg ctcaggctta caagacagca gcctaagtgg      780
ctgcccaggg ggttgggggg aagggagtt ggggttacgg tcgggattag ggggtggggg       840
gtggggcagc cttaacctct aatcaacctc aactagttca taagggtggg tagtgggggg     900
gactaggcag ccactttgtc actctcatgt cttctttaag gcatcgtttg tcagatagaa      960
tggtctcttg tggggtaggc cagtccttag cccaaaaggt ggaaagagca gtctctctga     1020
atcccaagtc agttctcata aaatagtcat aagacctagc ggcactcata gacatcaacc     1080
cttttgcttt agccctcttg tcccctttct tatcaagttt actcaaaacc aactcaactg     1140
ggcttatcga gaagtatatc atcagatggg tgtctctggt catcttagag aatgtcttag     1200
caaccagtct tgtcacccgt gctgcttgga ccacacagat gtctccaagg atgtcatttc     1260
ctgggagatc aaaagcagtc aatccgtgcg ctgcgccttc tatgagcact cgtctgtgaa     1320
tctccactat ctgctcctca ttagtggagt tgtaaagccc agaggcctta accagtaatt     1380
tcaggtatct ctggatagac cccgggtcaa actctgacaa gaacaggagc tcctcgaagt     1440
aatagtctat aaactctaga gtaggaatcc ctgtgggcca cctgagagca gacaaaaggt     1500
atctcttgtt gctcctcttt agttggtgaa tcgattcctg gtagagctct ctcatagttg     1560
gctcgtaaag tctggttcga actgcactga tcataccagg ccccagcaca gcaggaaact     1620
ccttctcaat gaggaaatgt gagagagttg gctttgactt atagaccacc ttataattgt     1680
ttatgtaaat ggggaactca ttctcaatca gagagcaatc cttctcaaaa tcaaggtgt      1740 ccaaatcaca gtctatgtag aacctgggca aagacctctt gtggcctgaa ccagatctat     1800
acttcaagat gacagctctg gattgcatgt taaccttgat aagcactagg gggtctttgt     1860
gt                                                                    1862
```

<210> SEQ ID NO 11
<211> LENGTH: 1862
<212> TYPE: DNA
<213> ORGANISM: Rift Valley fever virus

<400> SEQUENCE: 11

```
acacaaagct ccctagagat acaaacacta ttacaataat ggacaactat caagagcttg       60
cgatccagtt tgctgctcaa gcagtggacc gcaatgagat tgaacagtgg gtccgagagt      120
ttgcttatca agggtttgat gcccgtagag ttatcgaact cttaaagcag tatggtgggg      180
ctgactggga gaaggatgcc aagaaaatga ttgttctggc tctaactcgt ggcaacaagc      240
ccaggaggat gatgatgaaa atgtcgaaag aaggcaaagc aactgtggag ctctcatca       300 acaagtataa gctaaaggaa gggaatcctt cccgggatga gttgactcta tcacgagttg      360
ctgccgcctt ggctggctgg acatgccagg ctttggtcgt cttgagtgag tggcttcctg      420
tcactgggac taccatggac ggcctatccc ctgcataccc gaggcatatg atgcaccca       480 gctttgctgg catggtggat ccttctctac caggagacta tctaagggca atattagatg     540
ctcactctct gtatctgctg cagttctccc gggtcatcaa cccaaacctc cgaggtagaa     600
caaaagagga ggttgctgca acgttcacgc agccaatgaa tgcagcagtg aatagcaact     660
ttataagcca tgagaagagg agagaattct tgaaagcctt ggacttgtg gattccaatg      720 ggaagccgtc agctgctgtc atggcagccg ctcaggctta caagacagca gcctaagtgg     780
ctgcccaggg ggttgggggg aagggagtt ggggttacgg tcgggattag ggggtggggg      840
gtggggcagc cttaacctct aatcaacctc aactagttca taagggtggg tagtgggggg    900
```

```
gactaggcag ccactttgtc actctcatgt cttctttaag gcatcgtttg tcagatagaa    960
tggtctcttg tggggtaggc cagtccttag cccaaaaggt ggaaagagca gtctctctga   1020
atcccaagtc agttctcata aaatagtcat aagacctagc ggcactcata gacatcaacc   1080
cttttgcttt agccctcttg tccccttcct tatcaagttt actcaaaacc aactcaactg   1140
ggcttatcga gaagtatatc atcagatggg tgtctctggt catcttagag aatgtcttag   1200
caaccagtct tgtcacccgt gctgcttgga ccacacagat gtctccaagg atgtcatttc   1260
ctgggagatc aaaagcagtc aatccgtgct ttttgccttc tatgagcact cgtctgtgaa   1320
tctccactat ctgctcctca ttagtggagt tgtaaagccc agaggcctta accagtaatt   1380
tcaggtatct ctggatagac cccgggtcaa actctgacaa gaacaggagc tcctcgaagt   1440
aatagtctat aaactctaga gtaggaatcc ctgtgggcca cctgagagca gacaaaaggt   1500
atctcttgtt gctcctcttt agttggtgaa tcgattcctg gtagagctct ctcatagttg   1560
gctcgtaaag tctggttcga actgcactga tcataccagg ccccagcaca gcaggaaact   1620
ccttctcaat gaggaaatgt gagagagttg gctttgactt atagaccacc ttataattgt   1680
ttatgtaaat ggggaactca ttctcaatca gagagcaatc cttctcaaaa tcaaggtgt    1740 ccaaatcaca gtctatgtag aacctgggca aagacgccgc ggcgcctgaa ccagatctat   1800
acttcaagat gacagctctg gattgcatgt taaccttgat aagcactagg gggtctttgt   1860
gt                                                                  1862

<210> SEQ ID NO 12
<211> LENGTH: 46
<212> TYPE: DNA
<213> ORGANISM: Artificial Sequence
<220> FEATURE:
<223> OTHER INFORMATION: synthetic oligonucleotide

<400> SEQUENCE: 12
agttgttaac atggattact ttcctgtgat atctgttgat ttgcag                  46

<210> SEQ ID NO 13
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 13
ggtcaatccc tgcgaggatg gcctcag                                       27

<210> SEQ ID NO 14
<211> LENGTH: 27
<212> TYPE: DNA
<213> ORGANISM: Artificial Sequence
<220> FEATURE:
<223> OTHER INFORMATION: synthetic oligonucleotide

<400> SEQUENCE: 14
ctgaggccat cctcgcaggg attgacc                                       27

<210> SEQ ID NO 15
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 15
```
cgctactagt ctaatcaacc tcaacaaatc catc                                    34

<210> SEQ ID NO 16
<211> LENGTH: 58
<212> TYPE: DNA
<213> ORGANISM: Artificial Sequence
<220> FEATURE:
<223> OTHER INFORMATION: synthetic oligonucleotide

<400> SEQUENCE: 16
tgtcgttaac atggattaca aggatgacga cgataagatg gccagtgata ccccaggt        58

<210> SEQ ID NO 17
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 17
aggaactagt tcaagttttc ggcgggctct ttaaca                                  36

<210> SEQ ID NO 18
<211> LENGTH: 34
<212> TYPE: DNA
<213> ORGANISM: Artificial Sequence
<220> FEATURE:
<223> OTHER INFORMATION: synthetic oligonucleotide

<400> SEQUENCE: 18
gaagggtacc gctcggacca ccatccaggc gtag                                    34

<210> SEQ ID NO 19
<211> LENGTH: 36
<212> TYPE: DNA
<213> ORGANISM: Artificial Sequence
<220> FEATURE:
<223> OTHER INFORMATION: synthetic oligonucleotide

<400> SEQUENCE: 19
ggctaagctt atgaacaaca ggtggatcct ccacgc                                  36

<210> SEQ ID NO 20
<211> LENGTH: 39
<212> TYPE: DNA
<213> ORGANISM: Artificial Sequence
<220> FEATURE:
<223> OTHER INFORMATION: synthetic oligonucleotide

<400> SEQUENCE: 20
gggtggtacc gctccacttt cagagccttc gcaaagcag                               39

<210> SEQ ID NO 21
<211> LENGTH: 38
<212> TYPE: DNA
<213> ORGANISM: Artificial Sequence
<220> FEATURE:
<223> OTHER INFORMATION: synthetic oligonucleotide

<400> SEQUENCE: 21
tacaaagctt atgggagaga atgctgatgg tgaccagg                                38